United States Patent [19]
Weiner et al.

[11] Patent Number: 6,019,971
[45] Date of Patent: *Feb. 1, 2000

[54] TREATMENT OF AUTOIMMUNE ARTHRITIS BY ORAL ADMINISTRATION OF COLLAGEN

[75] Inventors: Howard L. Weiner, Brookline; David A. Hafler, W. Newton, both of Mass.

[73] Assignee: AutoImmune Inc., Lexington, Mass.

[*] Notice: This patent is subject to a terminal disclaimer.

[21] Appl. No.: 08/463,946

[22] Filed: Jun. 5, 1995

Related U.S. Application Data

[62] Continuation of application No. 08/328,562, Oct. 24, 1994, Pat. No. 5,869,093, which is a continuation of application No. 07/596,936, Oct. 15, 1990, abandoned, which is a continuation-in-part of application No. 07/460,852, filed as application No. PCT/US88/02139, Jun. 24, 1988, abandoned, which is a continuation-in-part of application No. 07/065,734, Jun. 24, 1987, abandoned.

[51] Int. Cl.$^7$ .......................... A61K 39/00; A61K 37/02; A61K 37/12
[52] U.S. Cl. .................................. 424/184.1; 424/185.1; 424/408; 424/409; 424/464; 514/2; 514/8; 514/21; 514/825
[58] Field of Search ............................. 424/184.1, 185.1, 424/408, 409, 464; 514/2, 8, 21, 825

[56] References Cited

U.S. PATENT DOCUMENTS

| | | | |
|---|---|---|---|
| 4,804,745 | 2/1989 | Koepff et al. | . |
| 5,075,112 | 12/1991 | Lane | . |
| 5,399,347 | 3/1995 | Trentham et al. | 424/184.1 |
| 5,720,955 | 2/1998 | Weiner et al. | 424/207.1 |
| 5,733,547 | 3/1998 | Weiner et al. | 424/184.1 |
| 5,783,188 | 7/1998 | Weiner et al. | 424/184.1 |

FOREIGN PATENT DOCUMENTS

| | | |
|---|---|---|
| 0 304 279 A2 | 2/1989 | European Pat. Off. . |
| 0 271 577 B1 | 10/1995 | European Pat. Off. . |
| WO 80/02501 | 11/1980 | WIPO . |
| WO 88/10120 | 12/1988 | WIPO . |
| WO 91/08760 | 6/1991 | WIPO . |
| WO 92/06708 | 4/1992 | WIPO . |
| WO 93/02699 | 2/1993 | WIPO . |

OTHER PUBLICATIONS

Wells, H., *J. Infect. Dis.* 9:147 (1911).
Ngan, J. et al., *J. Immunol.* 120:861 (1978).
Gautam, S. et al., *J. Immunol.* 135:2975 (1985).
Titus, R.G. et al., *Int. Arch. Allergy Appl. Immunol.* 65:323 (1981).
Nagler–Anderson, C. et al., *Proc. Natl. Acad. Sci. USA* 83:7443 (1986).
Swierkosz, J.E. et al., *J. Immunol.* 119:1501 (1977).
Lando, Z. et al., *Nature* 287:551 (1980).
Lando, Z. et al., *J. Immunol.* 126:1526 (1981).
Sriram, S. et al., *Cell. Immunol.* 75:378 (1983).
Alvord, E.C. et al., *Annals of Neurol.* 6:461 (1979).
Alvord, E.C. et al., *Annals of Neurol.* 6:469 (1979).
Alvord, E.C. et al., *Annals of Neurol.* 6:474 (1979).
Traugott, U. et al., *J. Neurol. Sci.* 56:65 (1982).
Raine, C.S. et al., *Lab. Invest.* 48:275 (1983).
McKenna, R.M. et al., *Cell. Immun.* 81:391 (1983).
Strejan, G.H. et al., *Cell. Immun.* 84:171 (1984).
McKenna, R.M. et al., *Cell. Immun.* 88:251 (1984).
Burns, J. et al., *Neurology* 36:92 (1986).
Belik, Y. et al., *Vopr. Med. Khim.* 24:372 (1978).
Braley–Mullen, H. et al., *Cell. Immun.* 39:289 (1978).
Kardys, E. et al., *J. Immunol.* 127:862 (1981).
Holoshitz, J. et al., *J. Immunol.* 131:2810 (1983).
Mokhtarian, F. et al., *Nature* 309:356 (1984).
McDermott, J.R. et al., *J. Neuro. Sci.* 46:137 (1980).
Raziuddin, S. et al., *J. Immunol.* 128:2073 (1982).
Alvord, E.C. et al., *Annals NY Acad. Sci.* 122:333 (1965).
Eylar, E.H. et al., *Nature* 236:74 (1972).
Schoen, R.T. et al., *J. Immunol.* 128:717 (1982).
Eylar, E.H., *Adv. Exp. Med. Biol.* 98:259 (1978).
Bitar, D.M., *Cell. Immunol.* 112:364 (1988).
Whitacre, C.C. et al., *Abs. 6th Int'l. Cong. Immunol.*, Toronto (Jul. 1986) (Dist. to Reg. Attendees Upon Request, May 1986).
Higgins, P.J. et al., *Annals Neurol.* 20:161 Abstract No. P154 (1986).
Whitacre, C.C. et al., Titles of Workshop Presentations, No. 615–09 *5th Int'l. Congr. of Immunol.*, Kyoto, Japan (1983).
Higgins, P.J. et al., *J. Neurolimmunol.* 16:77 (1987).
Gonsette, R.E. et al., *J. Neurol.* 216:27 (1977).
Myers, L.K. et al., *J. Immunol.* 143:3976 (1989).
Myers, L.K. et al., *J. Exp. Med.* 170:1999 (1989).
Lider, O. et al., *J. Immunol.* 142:748 (1989).
Higgins, P.J. et al., *J. Immunol.* 140:440 (1988).
Campbell, B. et al., *Arch. Neurol.* 29:10 (1973).
Trentham, D.E. et al., *J. Clin. Invest.* 66:1109 (1980).
Thompson, H.S.G. et al., *Clin. Exp. Immunol.* 64:581 (1985).
Mowat, A.M., *Immunol. Today* 8:93 (1987).
AutoImmune Press Release of May 12, 1997.
Allegreta, M., et al., *Science* 247:718, 1990.
Cremer, et al., *J. Immunol.* 87:2995, 1983.
Englert, et al., *Cell. Immunol.* 87:357, 1984.

(List continued on next page.)

*Primary Examiner*—Ponnathapura Achutamurthy
*Attorney, Agent, or Firm*—Darby & Darby

[57] ABSTRACT

The invention is directed to a method of treating a T cell-mediated autoimmune disease in animals, including humans, by the oral administration of autoantigens, fragments of autoantigens, or analogs structurally related to those autoantigens, which are specific for the particular autoimmune disease. The method of the invention includes both prophylactic and therapeutic measures.

20 Claims, 10 Drawing Sheets

OTHER PUBLICATIONS

Fritz et al., *J. Immunol.*, 134:2328–2332, 1985.
Fritz et al., *J. Immunol.*, 130:191–194, 1983.
Pettinelli et al., *J. Immunol.*, 129:1209–1211, 1982.
Whitaker et al., *J. Bio. Chem*, 250:9106–9111, 1975.
Thompson et al., *Clin. Exp. Immunol.*, 64:581–586, 1985.
Lider et al., *J. Immunol.*, 142:748–752, 1989.
Friedman et al., *PNAS*, 91:6688–6692, 1994.
Bitar, dissertation entitled, *The Suppressive Effects of Oral Myelin Basic Protein . . .* , 1986.
Nagler–Anderson, dissertation entitled, *Immunoregulation of an Exp. Model of Autoimmunity*, 1986.
Rothbart, *1st Forum in Virology*, pp. 518–520, 1986.
Bitar et al., *Cell. Immunol.*, 112:364–370, 1988.
Eylar et al., *Neurochem. Research*, 4:249–258, 1979.
Kagnoff, *Oral Tolerance*, pp. 248–269, 1982.
Mowat, *Immunol. Today*, 8:93–98, 1987.
Weiner et al., *Science*, 259:1321–1324, 1993.
Campbell et al., *Arch. Neurol.*, 29:10–15, 1973.
Carnegie et al.,*Immunol.* 19:55–63, 1970.
Fritz et al., *J. Immunol.*, 130:1024–1026, 1983.
Hashim et al., *Arch. Biochem. and Biophy.*, 156:287–297, 1973.

TREATMENT OF AUTOIMMUNE ARTHRITIS BY ORAL ADMINISTRATION OF COLLAGEN

This is a continuation of application Ser. No. 08/328,562, filed Oct. 24, 1994, now U.S. Pat. No. 5,869,093, which is a continuation of application Ser. No. 07/596,936, filed Oct. 15, 1990 (now abandoned), which is a continuation-in-part of Ser. No. 07/460,852 filed Feb. 21, 1990 (now abandoned) in turn the national stage of PCT/US88/02139, filed Jun. 24, 1988, which is a continuation-in-part of Ser. No. 07/065,734, filed Jun. 24, 1987 (now abandoned).

FIELD OF THE INVENTION

The present invention relates to the field of treatment of autoimmune diseases and in particular T cell-mediated or T cell-dependent autoimmune diseases. Specifically, the present invention provides the administration of autoantigens, or fragments or analogs thereof, for the prophylactic and therapeutic treatment of such autoimmune diseases.

BRIEF DESCRIPTION OF THE BACKGROUND ART

I. Autoimmune Diseases in General

Autoimmune diseases are caused by an abnormal immune response involving either cells or antibodies directed against normal tissues. A number of strategies have been developed to suppress autoimmune diseases, most notably drugs which nonspecifically suppress the immune response. A method of inducing immunologic tolerance by the oral administration of an antigen to prevent autoimmune responses was first demonstrated by Wells in 1911. Wells, H., *J. Infect. Dis.* 9:147 (1911). The oral induction of unresponsiveness has also been demonstrated for several T-cell dependent antigens. Ngan, J. et al., *J. Immunol.* 120:861 (1978), Gautam, S. et al., *J. Immunol.* 135:2975 (1985), Titus, R. et al., *Int. Arch. Allergy Appl. Immun.* 65:323 (1981). Antigen-driven peripheral immune tolerance by the oral route has recently been shown to serve as an effective immunoregulatory therapeutic approach in several experimental autoimmune diseases (Higgins, P. J., et al., *J. Immunol.* 140:440 (1988); Lider, O., et al., *J. Immunol.* 142:748–752 (1989); Bitar, D. M., et al., *Cell. Immunol.* 112:364 (1988); Nussenblatt, R. B., et al., *J. Immunol.* 144:1689 (1990); Nagler-Anderson, C., et al., *Proc. Natl. Acad. Sci. USA* 83:7443–7446 (1986); Thompson, H. S. G., et al., *Clin. Exp. Immunol.* 64:581–586 (1986)).

II. Experimental Allergic Encephalomyelitis

Scientists have also studied ways to suppress autoimmune diseases in various animal models. Experimental allergic encephalomyelitis (EAE) is a T cell-mediated autoimmune disease directed against myelin basic protein (MBP) and has been studied as a model for multiple sclerosis in several mammalian species. See, Alvord, E. et al., *Experimental Allergic Encephalomyelitis—A Useful Model For Multiple Sclerosis* (Allan R. Liss, New York, 1984). Immunoregulation of EAE is known to be at least partially dependent on suppressor T cells (Ts). It has been shown that Ts are present in rats which have recovered from EAE. Swierkosz, J. et al., *J. Immunol.* 119:1501 (1977). Furthermore, it has been shown that suppressor T cells account for the unresponsiveness to EAE that is exhibited by some mouse strains. Lando, Z. et al., *Nature* 287:551 (1980).

Various methods have been employed to induce antigen-specific suppression of EAE. For example, immunization with MBP emulsified in incomplete Freund's adjuvant, as shown by Lando, Z. et al., *J. Immunol.* 126:1526 (1981), and intravenous injection of MBP-conjugated lymphoid cells as shown by Sriram, S. et al., *Cell. Immunol.* 75:378 (1983) have been used.

Three papers by Alvord et al. are reported in *Annals of Neurology* in Vol. 6 at pp. 461–468, 468–473, and 474–482, respectively (1979). The first and second of these papers disclose the suppression of EAE in monkeys by the parenteral administration of MBP only when administered together with a nonspecific adjunctive factor, e.g., an antibiotic or a steroid. The third report discloses the presence in the cerebrospinal fluid of patients with multiple sclerosis of several proteases that degrade MBP to antigenically active peptide fragments.

Papers by Traugott et al., *J. Neurological Science* 56:65–73 (1982), and Raine et al., *Lab. Investigation* 48:275–84 (1983) disclose that treatment of a strain of guinea pigs suffering from chronic relapsing EAE by parenterally administered MBP alone or in incomplete Freund's adjuvant (IFA) or in combination with a lipid hapten of myelin, namely, galactocerebroside, suppressed the clinical symptoms of EAE.

Furthermore, McKenna et al., *Cell. Immun.* 81:391–402 (1983), discloses that preinjection of rats with guinea pig MBP coupled to syngeneic spleen leukocytes or to syngeneic red blood cells suppressed the subsequent induction of EAE using guinea pig MBP in Freund's complete adjuvant. The degree of suppression correlated positively with the amount of MBP administered.

A report by Strejan et al., *Cell. Immun.* 84:171–184 (1984), discloses that preinjection of rats with guinea pig MBP encapsulated within phosphatidylserine liposomes suppressed the clinical signs and symptoms of EAE that appear in rats injected with guinea pig MBP in complete Freund's adjuvant.

Another paper by McKenna et al., *Cell. Immun.* 88:251–259 (1984), discloses that the suppressive effects of injected guinea pig MBP leukocyte complexes disclosed in their 1983 report was abolished when animals were pretreated with cyclophosphamide, a drug that inhibits the production of suppressor T lymphocytes.

A report by Krasner et al., *Neurology* 36:92–94 (1986) discloses that synthetic C copolymer I, which is being tested as a treatment for multiple sclerosis because it protects animals against EAE, does not exhibit immunologic cross-reactivity with MBP.

Additionally, Belik et al., *Vopr. Ned. Khim.* 24:372–377 (1978), discloses the parenteral administration of "alkaline myelin protein fragment" and "synthetic encephalitogenic peptide" to guinea pigs with EAE. The animals recovered after administration of "alkaline myelin protein fragment" to the animals sensitized by bovine "alkaline myelin protein fragment" or by "synthetic encephalitogenic peptide."

Previous studies in EAE and EAU demonstrated that increasing dosages of MBP or S-Ag were associated with better disease protection (Higgins, P. J., et al., *J. Immunol.* 140:440 (1988); Nussenblatt, R. B., et al., *J. Immunol.* 144:1689 (1990)) and, in general, investigators have reported enhancement of oral tolerance by feeding larger amounts of antigen (Mowat, A. M., *Immunol. Today* 8:93 (1987)).

One report has suggested that EAE may be suppressed by adoptive transfer of $CD8^+$ T cells from orally tolerized animals (Lider, O., et al., *J. Immunol.* 142:748–752 (1989)).

However, it is not known in the art to successfully treat EAE after EAE manifests itself in the afflicted animal. Also, it is not known in the art to successfully treat multiple sclerosis after multiple sclerosis manifests itself in the patient. Thus a need still exists for a method of suppressing and treating multiple sclerosis.

III. Adjuvant Arthritis

Adjuvant arthritis (AA) is an experimental model of inflammatory joint disease and especially a model of rheumatoid arthritis. Adjuvant arthritis is induced by intradermal injection of a suspension of *Mycobacterium tuberculosis* (MT) in oil (Pearson, C. M., *J. Chronic Dis.* 16:863–874 (1963)). Between 10 and 15 days following injection, animals develop a severe, progressive arthritis.

Because of its resemblance to human rheumatoid arthritis in both clinical and histopathological features (Jasin, H. E., *Federation Proc.* 32:147 (1972)), AA has been used as a model to investigate mechanisms of immune mediated joint disease and to investigate methods for the treatment of an organ specific autoimmune disease.

Adjuvant arthritis is a cell mediated autoimmune disease and can be transferred by cell populations or by T cell clones specific for MT (Taurog, J. D. et al., *Cell. Immunol.* 75:271 (1983); Taurog, J. D. et al., *Cell. Immunol.* 80:198 (1983); Cohen, L. R. et al., *Arthritis and Rhem.* 28:841 (1985)). Studies have suggested that the primary autoantigen in adjuvant arthritis is a 65-kd mycobacterial heat shock protein (HSP) (van Eden, W. et al., *Nature* 331:171 (1988)). This protein also appears to be important in streptococcal cell wall arthritis (DeJoy, S. Q. et al., *J. Exp. Ned.* 170:369 (1989); van den Broek, M. et al., *J. Exp. Med.* 170:449 (1989)). Immunity to type II collagen has been shown to exist in adjuvant arthritis (Trentham, D. E. et al., *J. Clin. Invest.* 66:1109 (1980)).

Tolerization following oral and intravenous administration of collagen has been shown to suppress another type of arthritis termed collagen-induced arthritis (CIA). Suppression of CIA in DBA mice by orally administered type II collagens (CII) is dose-dependent with suppression observed when 0.5 mg but not 3 mg was given 8 times over a two-week period (Nagler-Anderson, C., et al., *Proc. Natl. Acad. Sci.* USA 83:7443–7446 (1986)). Similar results were reported for CIA in rats with greater protection when CII was given at 2.5 μg/g than 25 μg/g (Thompson, H. S. G., et al., *Clin. Exp. Immunol.* 64:581–586 (1986)). In terms of i.v. tolerization, 1 mg was given to suppress CIA in DBA mice (Myers, L. K., et al., *J. Exp. Med.* 170:1999 (1989)).

Adoptive transfer of protection for CIA arthritis has been reported for animals treated intravenously with CII (Myers, L. K., et al., *J. Immunol.* 143:3976 (1989)) but not for oral tolerization (Nagler-Anderson, C., et al., *Proc. Natl. Acad. Sci.* USA 83:7443–7446 (1986); Thompson, H. S. G., et al., *Clin. Exp. Immunol.* 64:581–586 (1986)).

However, it has not previously been known that oral administration of CII suppresses AA, the animal model for human rheumatoid arthritis, and that this suppression can be adoptively transferred by splenic T cells from CII fed animals. Thus a need exists for the treatment of autoimmune diseases, and especially for the treatment of T cell-mediated or T cell-dependent autoimmune disease.

SUMMARY OF THE INVENTION

The present invention provides methods for the treatment of a T cell-mediated or T cell-dependent autoimmune disease in a subject in need of such treatment, comprising the oral administration of autoantigens, fragments of autoantigens, or analogs structurally related to autoantigens specific for the particular autoimmune disease, to such subject, in an amount effective to treat the autoimmune disease.

Both the clinical and histological effects of such autoimmune diseases are suppressed in a dose-dependent manner by the methods of the invention. Moreover, such suppression occurs whether the administration of autoantigens occurs before or after onset of the autoimmune disease.

According to the methods of the invention, T cell-dependent autoimmune diseases are also suppressed by oral administration of non disease-inducing and disease-inducing fragments of the autoantigen. The oral administration of autoantigens, therefore, represents an effective, simple method by which an autoimmune disease can be naturally immunoregulated.

In an additional aspect of the invention, methods for the treatment and suppression of EAE and multiple sclerosis are provided, such methods providing the enteral administration of specific fragments of myelin basic protein to a subject in need of such treatment, such methods being useful before or after onset of the autoimmune disease.

In an additional aspect of the invention, methods for the treatment and suppression of adjuvant arthritis and rheumatoid arthritis are provided, such methods providing the enteral administration of type II collagen (CII) to a subject in need of such treatment, such methods being useful before or after onset of the autoimmune disease.

DESCRIPTION OF THE PREFERRED EMBODIMENTS

I. Definitions

Figure 1:
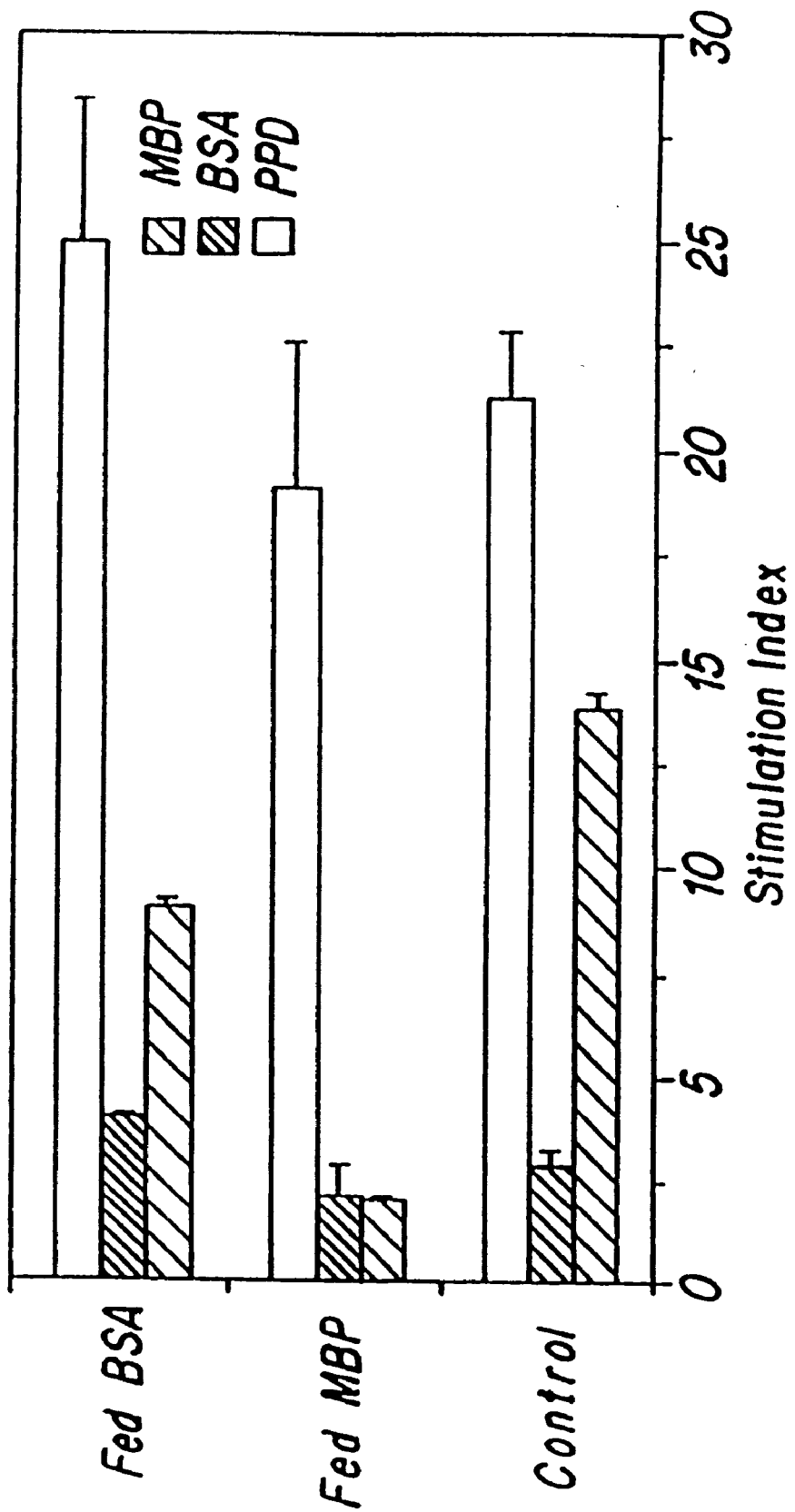
FIG. 1: antigen specificity of orally-induced suppression of the proliferative response in Lewis rats. Animals were fed 500 μg of MBP or BSA on days −7, −5 and −2, then immunized with 100 μg MBP in CFA on day 0. Nine days after immunization, lymph nodes were removed and proliferative response to MBP, BSA and PPD (all at 50 μg/ml) determined as described in Example 3. Stimulation index= experimental cpm/control cpm.

In the description that follows, a number of terms used in immunology are extensively utilized. In order to provide a clear and consistent understanding of the specification and claims; including the scope to be given such terms, the following definitions are provided.

Autoimmune disease. An autoimmune disease is a malfunction of the immune system of an animal, including humans, in which the immune system fails to distinguish between foreign substances within the animal and substances which are part of the animal's normal composition.

Autoantigen. An "autoantigen" is any substance normally found within an animal that, in an abnormal situation such as an autoimmune disease, is no longer recognized as part of the animal itself by the lymphocytes or antibodies of that animal, and is therefore attacked by the immunoregulatory system as though it were a foreign substance.

Biologically active fragments. The term "biologically active fragment(s)" of an autoantigen includes any partial amino acid sequence of an autoantigen that is capable of inducing the same biological response as the full-length autoantigen, i.e., the ability to suppress or eliminate T cell-mediated or T cell-dependent autoimmune response, upon oral introduction.

Analog. The term "analog(s)" of an autoantigen includes compounds that are so structurally related to the autoantigen that they possess the same biological activity as the autoantigen, i.e., the ability to eliminate or suppress the same or equivalent T cell-mediated or T cell-dependent autoimmune response, upon administration of the autoantigen. As such, the term includes amino acid sequences which differ from the amino acid sequence of the autoantigen by one or more amino acids (while still retaining substantially equivalent biological activity of the autoantigen) as well as chemical compounds which mimic the biological activity of the autoantigens in their ability to suppress or alleviate the symptoms of the disease. Such compounds may consist of tissue from a target organ that is the site of attack in an autoimmune disease.

Animal. The term "animal" covers all life forms that have an immunoregulatory system and are therefore susceptible to autoimmune diseases, including humans.

Treatment. The term "treatment" is meant to include both the prophylactic measures to prevent such autoimmune diseases as well as the suppression or alleviation of symptoms after the onset of such autoimmune diseases.

Administration. By the term "introduction" or "administration" of an autoantigen to a subject in need of treatment with such autoantigen is intended providing the autoantigen or its biologically active fragments, or biologically active analogs, to such subject in a manner which retains the therapeutic effectiveness of such autoantigen for a length of time sufficient to provide a desired beneficial effect to such subject. In a preferred embodiment, the autoantigen is introduced into the stomach of such subject by way of the mouth. However, by "oral," Applicants do not intend to limit administration to that provided per os and intend to include any administration which provides such autoantigens to the subject's stomach or digestive tract.

Type II collagen. Type II collagen ("CII") is the type of collagen found inter alia, in cartilage, the interverbebral disc and the vitreous body. Type II collagen contains three α1(II) chains ([α1(II)]$_3$).

As is known in the art, collagen is a family of fibrous proteins that have been classified into a number of structurally and genetically distinct types (Stryer, L. *Biochemistry*, 2nd Edition, W. H. Freeman & Co., 1981, pp. 184–199). Type I collagen is the most prevalent form and is found inter alia, in skin, tendons, cornea and bones and consists of two subunits of α1(I) collagen and one subunit of a different sequence termed α2. Other types of collagen, including type II collagen, have three identical subunits or chains, each consisting of about 1,000 amino acids. Type III collagen is found inter alia, in blood vessels, the cardiovascular system and fetal skin and contains three α1(III) chains ([α1(III)]$_3$). Type IV collagen is localized, inter alia, in basement membranes and contains three α1(IV) chains ([α1(IV)]$_3$).

The present invention relates to the treatment of T cell-mediated or T cell-dependent autoimmune diseases by the oral administration of autoantigens specific for such autoimmune diseases as well as biologically active fragments of the autoantigens, and analogs thereof.

The primary use of the invention is to treat a large category of diseases, prior to and/or after onset thereof, such diseases being collectively called autoimmune diseases, including but not limited to multiple sclerosis, myasthenia gravis, rheumatoid arthritis, diabetes mellitus and especially juvenile diabetes mellitus, systemic lupus erythematosus, autoimmune thyroiditis, autoimmune hemolytic anemia, and contact sensitivity disease, which may, for example, be caused by plant matter, such as poison ivy.

Thus, according to the methods of the invention, the autoimmune response which underlies multiple sclerosis may be treated by administration of MBP or biologically active portions thereof. Also, according to the methods of the invention, the autoimmune response which underlies rheumatoid arthritis may be treated by the administration of CII biological active portions thereof.

The present invention is based on the discovery and confirmation that the oral or enteral administration of MBP is an effective means of suppressing chronic and acute monophasic EAE. In a highly preferred embodiment, such administration is per os. The suppression of EAE by the enteral administration of MBP after manifestation of the disease is unexpected.

The present invention is further based on the discovery that the enteral administration of type II collagen is an effective way of suppressing adjuvant arthritis. The suppression of adjuvant arthritis by type II collagen is especially surprising because type II collagen is unexpectedly much more efficient at suppressing adjuvant arthritis than is MT. In a preferred embodiment, such administration is per os.

Enterally induced tolerance in both EAE and adjuvant arthritis is dose-dependent and both clinical and histological symptoms of the disease are lessened in severity. Because, for example, the oral administration of an irrelevant antigen such as bovine serum albumin (BSA) or another autoantigen such as collagen or "S" antigen (the autoantigen involved with experimental autoimmune uveitis) has no effect on susceptibility to EAE, it can be said that the oral induced tolerance to EAE is specific for MBP, the antigen to which the T cells that mediate the disease are sensitized.

Furthermore, the oral administration of MBP to rats induces the suppression of immune responses to MBP. For example, lymphoid cell proliferation and the production of anti-MBP antibodies are both decreased. The cells responsible for both the suppression of the disease and suppression of antigen-specific cellular responses in vitro are of T cell origin and are suppressor/cytotoxic $CD8^+$ T lymphocytes.

Thus, as demonstrated below, using the EAE animal model for multiple sclerosis and using the animal model for AA, the simple method of administration of autoantigens such as MBP or CII respectively, as taught by the invention, is an effective treatment to suppress the development of specific autoimmune disease, certain immune responses to the autoantigens, and the progression of the disease after such disease has manifested itself in a subject.

In general, the autoantigen, fragment, or analog is introduced orally in an amount of from one to 1000 mg per day, and may be administered in single dose form or multiple dose form. Preferably the autoantigen, fragment, or analog is administered in an amount of from 25 to 850 mg per day. As is understood by one skilled in the art, the exact dosage is a function of the autoantigen, the age, sex, and physical condition of the patient, as well as other concurrent treatments being administered. Such preparations may be administered to an animal in need of treatment for such autoimmune disease so as to ameliorate, relieve, alleviate, reverse, or lessen the severity of the disease. Such preparations may also be administered to an animal who is predisposed to developing such autoimmune disease so as to prevent the onset of such disease or to lessen the severity of such disease when it does emerge.

Where the autoantigen, fragment, or analog is introduced orally, it may be mixed with other food forms and consumed in solid, semi-solid, suspension, or emulsion form. Such autoantigen may be mixed with pharmaceutically acceptable salts, carriers, flavor enhancers, and the like.

An autoantigen may be administered in combination with any other appropriate autoantigen for administration to a subject in need of such autoantigen. For example, type II collagen(s) from more than one tissue source or species may be used. The autoantigens of the invention may also be administered in combination with any appropriate pharmacological carrier for administration to a subject in need of such autoantigen. Such autoantigens can be administered in any form that effects prophylactic, palliative, preventative or curing conditions of autoimmune disease in humans and animals.

The autoantigens of the invention can be employed in dosage forms such as tablets, capsules, powder packets, or liquid solutions for oral administration as long as the biological activity of the autoantigen is not destroyed by such dosage form.

Preparations of the autoantigens of the invention for oral administration include autoantigens provided as dry powders, food-stuffs, aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils.

Where the autoantigen, fragment, or analog is administered enterally, it may be introduced in solid, semi-solid, suspension or emulsion form and may be compounded with any of a host of pharmaceutically acceptable carriers, including water, suspending agents, emulsifying agents.

The autoantigens of the invention may also be administered by means of pumps, or in sustained-release form, especially, when administered as a preventative measure, so as to prevent the development of autoimmune disease in a subject or when administered to ameliorate or delay an already established autoimmune disease.

Pharmaceutical compositions which contain the autoantigen of the invention and which are useful in the methods of the invention are manufactured in a manner which is in itself known. For example, the autoantigens may be provided as a pharmaceutical composition by means of conventional mixing, granulating, dragee-making, dissolving, lyophilizing or similar processes. Such compositions, in and of themselves, find utility in the control of autoimmune disease be it chronic or acute.

Additionally, a low potency version of such compositions is useful in the management of mild, chronic, or acute autoimmune disorders.

Autoantigens which are substantially free of natural contaminants can be isolated and purified from their natural or recombinant sources in accordance with conventional conditions and techniques known in the art previously used to isolate such proteins, such as extraction, precipitation, chromatography, affinity chromatography, electrophoresis, or the like.

One of skill in the art can identify the antigenic domain(s) of an autoantigen using techniques known in the art, without undue experimentation, and such domains are preferred in the methods of the invention. For example, derivatives of the native autoantigens or, derivatives of recombinantly produced autoantigens can be made by proteolytic cleavage of a full-length protein with common proteases, such as, for example, trypsin, chymotrypsin, and subtilisin. Affinity chromatography with actin-derivatized resins may be used to assay such fragments for their autoimmune disease suppression ability.

When identification of compounds or fragments thereof which possess autoimmune disease suppression activity is desired, such compounds or fragments can also be identified using techniques known in the art.

Further, such fragments may be identified by their homology to other known autoantigenic domains wherein it may be predicted that function will follow homology.

For example, autoantigens useful in the methods of the invention may be identified by ability of such autoantigens to suppress such autoantigen-induced autoimmune disease upon administration of such autoantigen to a subject afflicted with or predisposed to the autoimmune disease. In the methods of the invention, autoimmune disease may be suppressed by such administration of autoantigen either prior to or after appearance of disease symptoms.

Having now generally described the invention, the following examples further describe the materials and methods used in carrying out the invention. The examples are not intended to limit the invention in any manner.

EXAMPLES

A. Methodology

Animals: Female Lewis or Wistar Furth rats weighing 150 to 220 g (6–8 weeks of age) were obtained from Charles River Laboratory, Wilmington, Mass., or from Harlan Sprague Dawley, Inc., Indianapolis, Ind., and used in all experiments.

Immunization of Animals: Rats were immunized in both hind footpads with 50 µg guinea pig MBP emulsified in complete Freund's adjuvant (CFA). In some experiments, 50 µg ovalbumin (OVA) (Sigma) was added to the emulsified antigens and injected similarly. EAE was characterized by limb paralysis and scored as follows: 0) no disease; 1) decreased activity, limp tail; 2) mild paralysis, unsteady gait; 3) moderate paraparesis, limbs splayed apart; and 4) tetraplegia.

Induction of Oral Tolerance: Rats were fed MBP or bovine serum albumin (BSA) five times at three-day intervals 1 mg in 1 ml PBS (8 gm NaCl 0.2 gm KCl, 1.44 gm of $Na_2HPO_4$, 0.24 gm of $KH_2PO_4$ in 1000 ml of $H_2O$) using a 23-gauge needle covered with plastic tubing.

Proliferation Assay: Nine days after immunization, the rats were sacrificed and their popliteal lymph nodes were removed. A single cell suspension was prepared by pressing is the lymph nodes through a stainless steel mesh. A total of $10^5$ lymph node cells (LNC) were cultured with the indicated number of either irradiated (2000 Rads) or intact LNC derived from fed rats in quadruplicate in round-bottomed 96-well plate (Costar). MBP and *Mycobacterium tuberculosis* (Mt), 50 µg/ml were added to the culture in a volume of 20 µl. The cultures were incubated for 80 hours and were pulsed with 1 µCi [$^3$H] TdR/well for the last 16 hours of culture. The cultures were then harvested on an automatic cell harvester and read on a standard liquid scintillation counter.

Percent suppression of primed LNC (PLNC) proliferation was calculated by the following formula:

$$\% \text{ Suppression} = 100 \times 1 - \frac{\text{cpm (irradiated LNC from fed rat + PLNC + antigen)}}{\text{cpm (irradiated LNC from untreated rat + PLNC antigen)}}$$

Proliferation Media: RPMI (Gibco) was used in all the experiments. The medium was filtered sterile after adding 2× $10^{-5}$M 2-mercaptoethanol, 1% sodium pyruvate, 1% penicillin and streptomycin, 1% non-essential amino acids, and 1% autologous serum.

Purification of Different Cell Subsets: For depletion of CD3, CD4, and CD8 populations from spleen cells, negative selection was used. Petri dishes were coated overnight at 4° C. with 10 ml of 1/1000 goat anti-mouse IgG+IgM antibodies (Tago) in PBS/BSA. The plates were then washed and coated with 3% fetal bovine serum in PBS for 30 min at 20° C. and washed again. Lewis LNC were stained with mouse anti-rat monoclonal antibodies (Serotec/Bioproducts) for CD3 (MRC, OX/38), CD4 (W 3/25), or CD8 (OX/8) diluted 1/100 in PBS. The cells were stained for 30 min on ice, washed, and seeded on the precoated petri dishes, 15 million cells/5 ml PBS/plate, at 4° C. The supernatant containing nonadherent cells was aspirated gently 60 minutes later and centrifuged twice before cell examination and counting. This protocol yields cell populations of about 85–95% purity as examined in the fluorescence activated cell sorter by examining membrane immunofluorescence.

Adoptive Transfer Experiments: Donor rats were fed with either MBP or BSA, 1 mg×5 times, at 3–4 day intervals and sacrificed 4 days after the final feeding. Mesenteric LNC and spleen cells were harvested and injected intraperitoneally either immediately or after activation with concavalin-A (Con-A), 1.5 µg/ml, in proliferation media for 48 hrs. The number of cells injected for adoptive transfer experiments were as follows: $120 \times 10^6$ for whole LNC population, either activated or not; $60 \times 10^6$ for CD3 depleted LNC; $80 \times 10^6$ for CD4 depleted population; and $95 \times 10^6$ for CD8 depleted LNC. Recipient Lewis rats were immunized with BP/CFA 4 hrs later for the induction of EAE.

Serum Levels of Antibodies: A solid-phase enzyme-linked immunoabsorbent assay (ELISA) was used for determination of antibody titers against MBP and OVA. Microtiter plates were incubated with 0.1 ml per well of 10 µg antigen/ml in doubled distilled water. Plates were incubated for 18 hrs at 25° C. After 3 washes with PBS/tween-20 (Bio-Rad), pH 7.5, plates were incubated with 3% BSA/PBS for 2 hrs at 37° C., washed twice, and 100 µl of diluted serum was added in quadruplicate. The plates were incubated for 2 hrs at 37° C. After three rinses with PBS/tween-20, plates were incubated with 100 µl/well of peroxidase-conjugated goat anti-rat IgG antibody (Tago, USA) diluted 1:1000 in 1% BSA/PBS for 1 hr at 25° C. Color reaction was obtained by exposure to D-phenylenediamine (0.4 mg/ml phosphate) citrate buffer, pH 5.0) containing 30% $H_2O_2$. The reaction was stopped by adding 0.4N $H_2SO_4$ and OD 492 nm was read on an ELISA reader.

In Vitro Measurement of Antibody Production: Popliteal and splenic LNC were obtained from fed, naive and challenged rats and seeded at a concentration of $10^7$ cells per ml petri dish either alone or irradiated (2000 Rads) together with other PLNC as indicated. The cultures were maintained in proliferation media, with or without antigen (20 µg/ml), for 3 days in an incubator and then harvested. The diluted supernatants were used to examine the in vitro production and secretion of IgG antibody and were measured for antibody production using an ELISA test as described previously.

Identification of Different Regions of the Myelin Basic Protein Molecule Responsible for Suppression of EAE: Overlapping fragments of the 1–37 region of guinea pig myelin base protein were synthesized using solid phase peptide technique. Houghten, R., *Proc. Natl. Acad. Sci.* USA 82:5131–5135 (1985). These fragments were then administered orally in equimolar concentrations to 15 mg of whole myelin basic protein They were administered on day −7, −5, and −2 prior to immunization. Animals were then challenged with basic protein in Freund's adjuvant according to established procedures and scored.

Demonstration that Oral Route of Administration of a Protein Antigen Determines to Which Fragment There Is an Immune Response: Animals were given whole myelin basic protein, either immunized in the foot pad with Freund's adjuvant or administered orally. Seven to 10 days thereafter, spleen and lymph node cells were removed and restimulated in vitro with different fragments of the myelin basic protein molecule.

Collagens and Adjuvant: Soluble-form chicken type II collagen was obtained from Genzyme Corporation, Boston, Mass. Bovine type III collagen was purchased from Southern Biotechnology Associates, Inc., Birmingham, Ala., whereas the type I collagen was a gift from Dr. O. Trentham, Beth Israel Hospital, Boston, Mass. *Mycobacterium tuberculosis* and incomplete Freund's adjuvant (IFA) were purchased from Difco Laboratories, Detroit, Mich. Complete Freund's adjuvant (CFA) was prepared by mixing IFA and MT ground to a fine powder.

Oral Administration Protocol: Antigens were orally administered in a 1 ml volume through a syringe fitted with 18G ball-point needle three times (on days −7, −5 and −2) before induction of disease. Collagens were dissolved in potassium phosphate buffer (pH 7.6) whereas MT was suspended in phosphate-buffered saline (PBS) for the feedings.

Induction of Arthritis: Adjuvant arthritis was induced in animals by intradermal injection at the base of the tail with 0.1 ml CFA containing 10 mg/ml *M. tuberculosis*.

Evaluation of Arthritis. The incidence of arthritis was defined as the number of rats that had clinical evidence of arthritis within 35 days after induction of disease. The severity of arthritis was graded according to standard methodology (Trentham, D. E. et al., *J. Exp. Med.* 146:857 (1977)). Each of the four paws was graded as follows: 0=normal, 1=redness only, 2=redness plus mild swelling, 3=severe swelling, 4=joint deformity. The arthritis score for each animal was the sum of the score for each of the four paws. The maximum arthritis score was the highest score of an individual animal during the entire course of the disease. All evaluations were performed in a blinded fashion without knowledge of the treatment group.

Lymphocyte Proliferation Assay: Rats were primed with 0.1 ml CFA containing 1 mg/ml MT at the base of the tail. Nine days later, the draining lymph nodes were removed and single cell suspensions were prepared. After being washed twice, the cells were resuspended in RPMI 1640 containing 1% glutamine, 1% penicillin/streptomycin, 1% nonessential amino acids, 5% fetal calf serum and $5\times10^{-5}$M 2-mercaptoethanol. The cells were then seeded into a 96-well flat-bottom plate in quadruplicate at the concentration of $2.5\times10^5$ cells/well and cultured with various concentrations of MT at 37° C. with 5% $CO_2$ for 72 hours. Tritiated thymidine was then added to the culture at 1 $\mu$Ci/well. The cells were harvested 6 hours after the pulsing and proliferation was determined by tritiated thymidine incorporation as measured by liquid scintillation counting.

Delayed-type Hypersensitivity (DTH) Responses: DTH responses were measured 30 days after the immunization. Rats were injected subcutaneously in both ears with either 10 $\mu$g of MT of 20 $\mu$g CII in 50 $\mu$l PBS. Ear swelling consisted of the difference in ear thickness measured before and 48 hours after the injection using micrometer caliper. DTH responses were also performed in unimmunized animals and animals fed CII only.

Adoptive Transfer of Suppression: Donor rats were fed three times with 3 $\mu$g of CII at 2–3 day intervals. Their spleens were removed 7 days after the last feeding and a single cell suspension was prepared. After lysis of the red blood cells with tris-$NH_4Cl$, ph 7.26 the splenocytes were washed twice in Hank's balanced salt solution (HBSS). In some experiments the splenocytes were further separated into T or B cell enriched populations by using nylon wool columns. $1\times10^8$ cells were injected intraperitoneally to each recipient, which were then injected with CFA to induce arthritis either on the same day or 2 days later. Splenocytes from unfed normal rats served as a control.

Example 1

Effect of Feeding MBP and Fragments Thereof

The effect of feeding MBP and its peptic fragments on the susceptibility to and severity of acute monophasic EAE was studied in the Lewis rat. Results show that this natural route of tolerance induction suppresses both the development of disease and immune responses to MBP.

To orally induce suppression of EAE, Lewis rats were fed MBP purified from guinea pig brain (Diebler, G., et al., *Prep. Biochem.* 2:139 (1972)) using a syringe equipped with a 20G ball point needle. Control animals were fed equal amounts of bovine serum albumin (BSA) or saline alone. EAE was induced by immunization with 50 $\mu$g MBP emulsified in complete Freund's adjuvant (CFA) containing 200 $\mu$g *Mycobacterium tuberculosis* by injection into the hind footpads. Disease was characterized by hind limb paralysis and incontinence usually between days 12 and 15 after immunization and in all cases rats recovered by day 16. The first series of experiments investigated the effect of number of feedings and dose of MBP on disease expression. Rats were fed various amounts of MBP either once 7 days before (day −7) the day of immunization (day 0) or three times on days −14, −7 and 0. The results (Table I) demonstrate that feeding MBP to rats suppresses EAE and that orally-induced suppression is dose-dependent. Multiple 500 $\mu$g feedings resulted in complete suppression of disease and were more effective than a single feeding at this dose. In addition to clinical manifestation of EAE, histological evidence of disease in rats was examined. Sixteen days after immunization, rats were sacrificed and brains removed and fixed in formalin solution. Fixative was a solution of 100 ml 70% ethanol, 10 ml 37% formalin and 5 ml glacial acetic acid. Slides of paraffin-embedded tissue were prepared from each rat and stained with hematoxylin and eosin. Perivascular inflammatory foci were quantified on coded slides by established procedures (Sobel, R., et al., *J. Immunol.* 132:2393 (1984)). As shown in Table I, feeding rats 500 $\mu$g MBP on days −14, −7 and 0 caused a marked decrease in the number of inflammatory lesions in the brain. A moderate decrease was found in animals fed 100 $\mu$g and no significant reduction of inflammation was found in rats fed 25 $\mu$g MBP.

Example 2

Effect of Prior Exposure to Antigen on Suppression

A second series of experiments investigated the effect of feeding MBP prior to or subsequent to immunization with MBP to determine whether the effectiveness of orally-induced suppression is affected by prior exposure to antigen. For these experiments, animals were fed 500 $\mu$g MBP three times either before or after active induction of disease (immunization with MBP). The results (Table II) demonstrate that the clinical expression of disease is suppressed whether animals were fed MBP before or after sensitization, the effect being more complete when antigen was fed prior to immunization. However, histologic examination revealed a dramatic reduction of perivascular infiltrates in rats fed MBP either before or after sensitization to MBP. Greater than 60% suppression of disease also occurred when rats were fed three times beginning on days +5 or +7 after immunization (data not shown).

In addition, experiments were performed in which rats were fed 100 $\mu$g of MBP at various times, before and after immunization, with MBP. As shown in Table III, disease suppression is seen with single feedings before or after immunization.

Example 3

Effect of Oral Administration of MBP on Cellular and Hormonal Immune Responses to MBP The effects of oral administration of MBP on cellular and humoral immune responses to MBP were also examined.

Proliferative responses to MBP were studied after feeding rats different doses of MBP and following feeding at different times with respect to immunization. Ten days after immunization, rats were sacrificed and single cell suspensions of draining (popliteal) lymph nodes prepared. Cells were cultured in microwells for 4 days, the final 24 hours with $^3$H-thymidine added. A volume of 0.2 ml containing $4 \times 10^5$ cells in RPMI 1640 containing 2% glutamine, 1% penicillin/streptomycin, $5 \times 10^{-5}$M 2-mercapto-ethanol and 5% fetal calf serum was added to each microwell and MBP added at 50 μg/ml. Wells were pulsed with 1 μCi tritiated thymidine, harvested onto fiberglass filters using a multiharvester and counted using standard liquid scintillation techniques.

Results (Tables I and II) demonstrate that feeding MBP causes a pronounced (75–92%) decrease in proliferative responses to MBP. Suppression of proliferation, unlike suppression of disease, occurred at all doses and feeding regimens tested, including feeding after immunization. Orally-induced suppression of the proliferative response to MBP is antigen-specific, as shown in FIG. 1. Specifically, feeding MBP does not suppress the proliferative response to purified protein derivative (PPD), an antigen derived from *M. tuberculosis* that induces a proliferative response as a consequence of immunization with CFA. Feeding an irrelevant antigen, BSA, does not affect the proliferative response to PPD and only slightly suppresses the proliferative response to MBP.

Example 4

Effect of Feeding MBP on the Production of Antibody to MBP

The effect of feeding MBP on the production of antibody to MBP was also examined. Rats fed MBP were immunized and blood removed by cardiac puncture 16 days following immunization. Levels of anti-MBP antibody in the serum were measured by ELISA. A volume of 0.1 ml of MBP solution (0.05 mg/ml in PBS) was added per microwell and incubated for 3 h at 37° C. Wells were washed with PBS containing 0.05% Tween (PBST) and blocked overnight at 4° C. with 5% BSA in PBS, pH 9.0. After washing wells with PBST, diluted rat sera were added and incubated for 3 h at r.t. and after washing with PBST secondary antibody (peroxidase conjugated goat anti-rat) added for 1 h at r.t. Substrate was added and the reaction was stopped with 0.1M NaFl. Plates were read at 450 nm on a Titertek multiscan. $Abs_{450}$ was also determined for serum from rats immunized only with CFA and was subtracted from all values as background.

Unlike suppression of proliferative responses which occurred at virtually all doses and feeding regimens tested, suppression of antibody production was only observed when animals were fed the highest dose tested (500 μg) on days −14, −7, and 0 (66% suppression, Table I). Of note is the lack of suppression in rats fed 500 μg MBP on days −7, −5 and −2 (Table II) suggesting that the temporal sequence in which an identical dose of MBP is fed is important in suppression of antibody responses.

TABLE I

Effect of Feeding Dose on Orally-Induced Suppression of EAE in Lewis Rats

| | Induction of EAE | | Immune Response to MBP (percent inhibition) | |
|---|---|---|---|---|
| | [a]Clinical Disease | [b]Histologic Score | [c]Proliferation | [d]Antibody |
| Immunized Controls Fed day −7 | 19/22 | 9.2 ± 5.8 | — | — |
| 25 μg | 3/5 | ND | 75.6 ± 2 | ND |
| 100 μg | 2/5[e*] | ND | 88.9 | ND |
| 500 μg | 3/10*** | ND | 88.9 ± 2 | ND |
| Fed days −14,−7,0 | | | | |
| 25 μg | 3/5 | 7.2 ± 5.2 | 82.1 | −48 ± 72 |
| 100 μg | 2/5* | 3.2 ± 1.9 | 80.8 ± 5 | 14 ± 49 |
| 500 μg | 0/10*** | 0.2 ± 0.4 | 87.2 ± 1 | 66 ± 39 |

(a) Rats were fed various doses of MBP on the indicated days and immunized with 50 μg MBP in CFA (200 μg M. tuberculosis on day 0. Shown are the number of diseased rats of the total number immunized. Immunized controls were fed BSA or saline.
(b) Rats were sacrificed on day 16 after immunization and brains removed and fixed. Shown are the average number of perivascular inflammatory foci per animal +/− s.d. ND = not determined.
(c) Proliferative response to MBP was measured for draining lymph node cells ten days after rats were immunized. A volume of 0.2 ml containing 4 × $10^5$ cells in RPMI 1640 containing 2% glutamine, 1% penicillin/streptomycin, 5 × $10^5$ M 2-mercapto-ethanol and 5% fetal calf serum was added to each microwell and MBP added at 50 μg/ml. Wells were pulsed with 1 μCi tritiated thymidine, harvested onto fiberglass filters using a multiharvester and counted using standard liquid scintillation techniques. Shown is the percentage inhibition of proliferative response to MBP with respect to the immunized control group. Average stimulation index of the immunized controls (MBP-stimulated cpm/background cpm) was 6.0 (29,888 cpm/4960 cpm).
(d) Rats were sacrificed on day 16 and blood drawn by cardiac puncture. Sera were diluted 1/15,625 in PBS and anti-MBP antibody levels were determined by ELISA. A volume of 0.1 ml of MBP solution (0.05 mg/ml in PBS) was added per microwell and incubated for 3 h at 37° C. Wells were washed with PBS containing 0.05% Tween (PBST) and blocked overnight at 4° C. with 5% BSA in PBS, pH 9.0. After washing wells with PBST, diluted rat sera were added and incubated for 3 h at room temperature and after washing with PBST secondary antibody (peroxidase conjugated goat anti-rat) added for 1 h at room temperature. Substrate was added and the reaction was stopped with 0.1 M NaFl. Plates were read at 450 nm on a Titertek multiscan. $Abs_{450}$ was also determined for serum from rats immunized only with CFA and was subtracted from all values as background. Shown is the percentage decrease in antibody level, as measured by absorbance of peroxidase substrate at 450 nm, with respect to immunized controls (Mean absorption at $A_{450}$ of immunized controls with background subtracted was 0.148).
(e) Groups were compared by chi-square analysis with one degree of freedom: * p < .05,  p < 0.1, * p < .001.

TABLE II

Effect of Feeding MBP to Rats Before or After Immunization on the Development of EAE

| | Induction of EAE | | Immune Response to MBP (percent inhibition) | |
|---|---|---|---|---|
| | [a]Clinical Disease | [b]Histologic Score | [c]Proliferation | [d]Antibody |
| Immunized Controls Days fed 500 μg MBP | 23/26 | 21.6 ± 5.1 | — | — |
| −7,−5,−2,+2,+5,+7 | 0/5 | 0.2 ± 0.4 | ND | 34 |
| −7,−5,−2 | 0/17 | 0 | 92.6 | 15 |
| +2,+5,+7 | 4/10** | 1.4 ± 2.3 | 91.5 ± 3 | 15 |

(a) Rats were fed 500 μg MBP on the indicated days and immunized with 50 μg MBP in CFA on day 0. Immunized controls were fed BSA or saline.
(b) See Table I.
(c) See Table I. Average stimulation index of immunized controls was 9.4 (82,247 cpm/8,718 cpm).
(d) See Table I. Mean absorption at $A_{450}$ of immunized controls with background subtracted was 0.403.
(e) See Table I.

TABLE III

Orally Induced Supression of EAE in Lewis Rats

| Feeding Schedule | # Rats Sick/Total |
|---|---|
| None | 11/16 |
| −14, −7, 0, +7 | 0/13 |
| −14 | 1/5 |
| −7 | 0/5 |
| 0 | 1/5 |
| +7 | 1/5 |

Rats were fed 100 μg MPB on the indicated days (with respect to day of immunization = 0), and immunized with 50 μg MBP with CFA (.5 mg/ml M. tuberculosis).

Example 5

Persistence of Orally-Induced Protection Against EAE

Further experiments were conducted to determine the persistence of orally-induced protection against EAE. After feeding on days −7, −5 and −2 with 500 μg MBP rats were immunized at various lengths of time after the last feeding. EAE was completely suppressed in rats for up to four weeks after feeding, and by eight weeks 50% of rats fed MBP were again susceptible to disease. The results are shown in Table IV, which indicates that tolerance to the disease is maintained for at least four weeks after the last feeding, with susceptibility to disease induction becoming apparent at eight weeks following feeding.

TABLE IV

Persistence of Orally Induced Tolerance of Lewis Rats

| Control Fed | | # Rats Sick/Total 9/14 |
|---|---|---|
| Immunized | day 0 | 0/4 |
|  | day +7 | 0/4 |
|  | day +14 | 0/4 |
|  | day +28 | 0/3 |
|  | day +56 | 4/8 |

Rats were fed 500 μg MBP on days −7, −5, and −2 and immunized on the indicated days with 50 μg MBP in CFA. Control rats (fed BSA) were likewise immunized.

Example 6

Effect of Fragments of MBP on the Development of EAE

It is known that the encephalitogenic region of guinea pig MBP in rats is a specific decapeptide sequence located at residues 75–84, which by itself can induce EAE, whereas other regions of the molecule are non-encephalitogenic (Hashim, G., *Myelin: Chemistry and Biology,* Alan R. Liss, N.Y. (1980)). Furthermore, for other antigens, it has been reported that distinct suppressor determinants exist at sites different from immunogenic determinants (Yowell, R., et al., *Nature* 279:70 (1979)). It was therefore investigated whether both encephalitogenic and non-encephalitogenic fragments of MBP could prevent EAE via oral administration. Fragments of guinea pig MBP were generated by limited pepsin digestion and separated by column chromatography (Whitaker, J., et al., *J. Biol. Chem.* 250:9106: (1975)). The three different fragments were fed to rats, then animals were immunized with whole MBP. It was found that both the disease-inducing (fragment 44–89) and non-encephalitogenic (fragments 1–37 and 90–170) peptides suppressed EAE when fed to rats, the non-encephalitogenic fragments being more effective in suppressing the disease than the encephalitogenic fragment (Table V). A decapeptide (S79) was synthesized which differs from the encephalitogenic sequence (residues 75–84) by a single amino acid substitution and is reported to induce suppression when injected into rats with CFA (Kardys, E., et al., *J. Immunol.* 127:862 (1981)). When S79 (Ala-Gln-Gly-His-Arg-Pro-Gln-Asp-Glu-Gly) was fed to animals it was also found to suppress EAE (Table V). Bovine MBP, which differs from guinea pig MBP at several sites including the encephalitogenic sequence and is not encephalitogenic in rats at doses encephalitogenic for guinea pig MBP (Holoshitz, J., et al., *J. Immunol.* 131:2810 (1983)), also suppressed disease when fed to animals prior to immunization.

TABLE V

The Effect of Feeding Encephalitogenic and Non-Encephalitogenic Fragments on the Development of EAE in Lewis Rats

|  | Clinical Incidence of EAE |
|---|---|
| Immunized Controls | 19/25 |
| MBP fragment 1–37 (109 μg) | 0/9[a]** |
| MBP fragment 44–89 (135 μg) | 3/11** |
| MBP fragment 90–170 (235 μg) | 0/4** |
| Peptide S79 (30 μg) | 1/8*** |
| Bovine MBP (500 μg) | 0/10*** |

Lewis rats were fed the indicated amounts of MBP fraqments or peptides (equimolar to 500 μg whole guinea pig MBP) on days −7, −5 and −2 and immunized on day 0 with 50 μg guinea pig MBP with CFA. Shown are the number of diseased rats of the total number immunized. (a) Groups were compared to immunized controls by chi-square analysis:  p < .01, * p < .001.

Example 7

Suppression of Adjuvant Induced Arthritis by Feeding Mycobacteria

Figure 2:
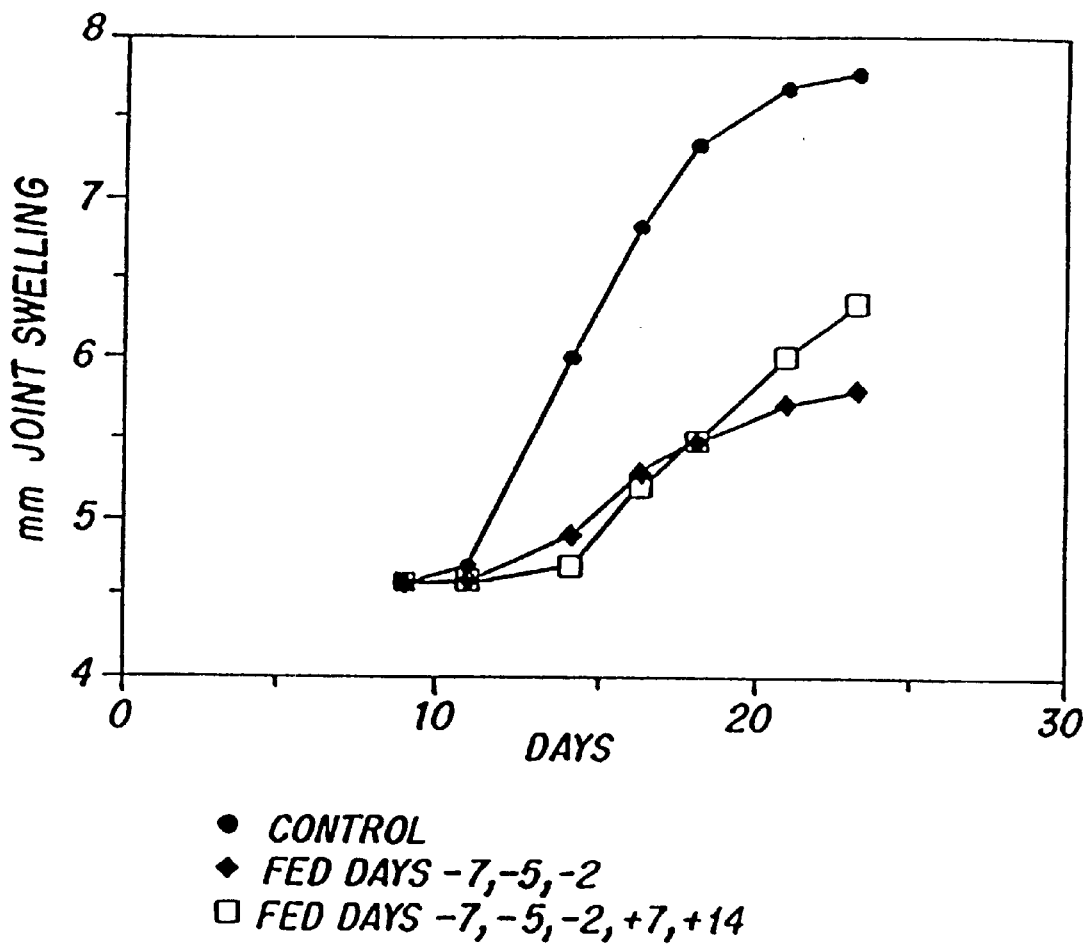
FIG. 2: orally induced suppression of adjuvant arthritis, as measured by joint swelling.

Adjuvant arthritis was induced in female Lewis rats by immunization with 0.1 ml of 10 mg/ml of complete Freund's adjuvant in the base of the tail. Animals were fed 2.0 mg of *Mycobacteria tuberculosis* in phosphate buffered saline on days −7, −5, and −2 prior to immunization on day 0 and subsequent to immunization on days +7 and +14. Arthritis was quantitated by measuring joint swelling for three weeks following immunization (Table VI and FIG. 2). Subsequent studies have indicated that while the results shown in FIG. 2 are occassionally obtained, in most instances, adjuvant arthritis was not suppressed by feeding animals *Mycobacteria tuberculosis*. Therefore, the ability to suppress adjuvant arthritis with *Mycobacteria tuberculosis* administration is highly variable. The reason for this variability is unknown.

TABLE VI

|  | Joint swelling (mm) on day 21 |
|---|---|
| Control | 7.61 ± 1.4 |
| Days Fed Mycobacteria |  |
| −7, −5, −2 | 5.61 ± 1.1* |
| −7, −5, −2, +7, +14 | 6.07 ± 0.9* |

Joint swellin = thickness of joint on day measured
*p < 0.01 compared to control (representative experiment of 4 animals/group)

Example 8

An Adoptive Transfer Model of EAE in the SJL Mouse

Figure 3:
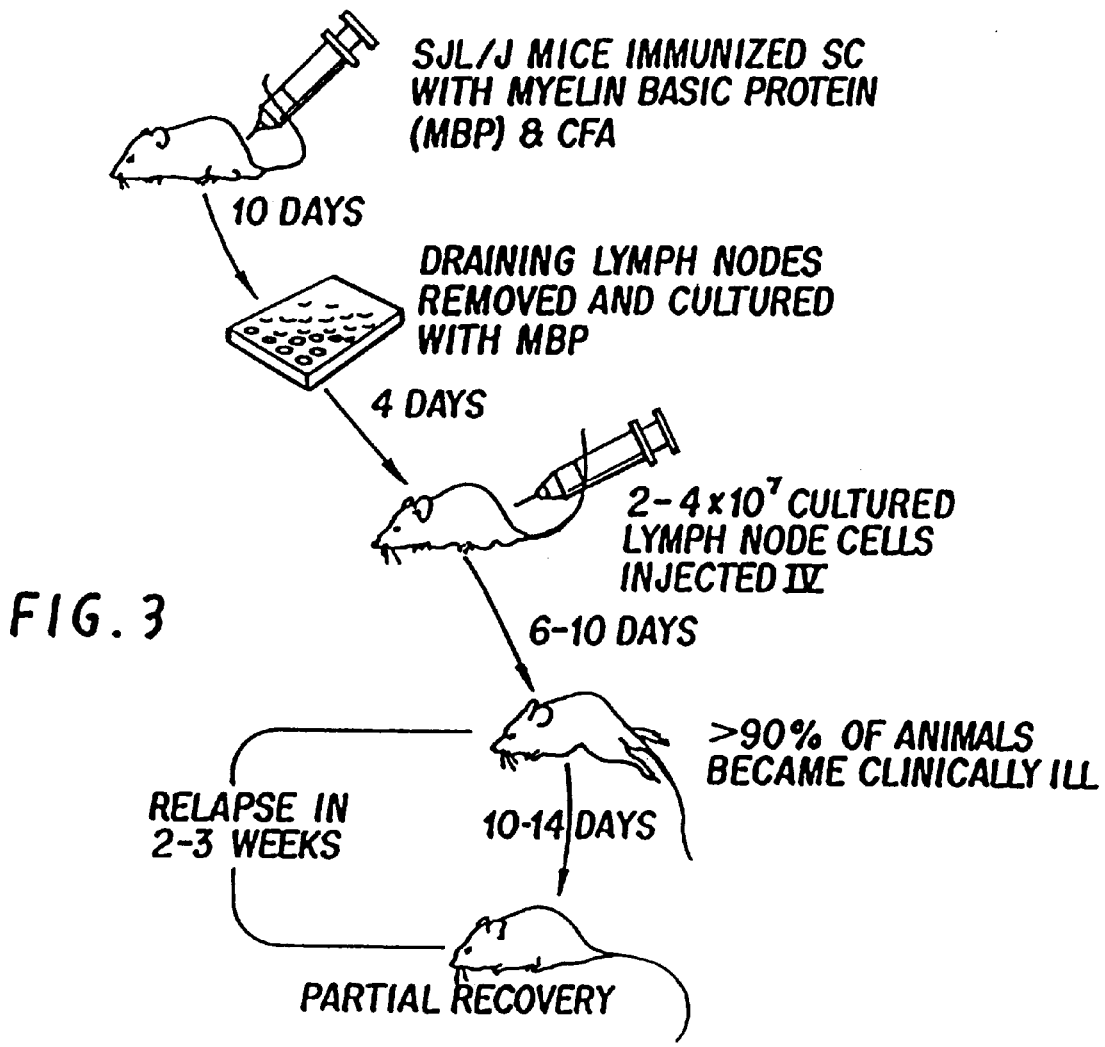
FIG. 3: protocol for inducing relapsing murine EAE.

A workable, reproducible model of adoptive relapsing EAE was established in the SJL mouse. The protocol for this model was adopted from Mokhtarian, et al., *Nature* 309:356 (1984). This protocol is depicted graphically in FIG. 3. Briefly, donor animals are immunized with an emulsion containing 400 μg of MBP and 30 μg of *M. tuberculosis* in CFA. Ten days thereafter, draining lymph nodes are removed and cultured with 50 μg/ml of MBP for four days, washed extensively, and 4–6×10$^7$ viable cells are injected intravenously into female recipient animals. Animals are scored for clinical EAE using standard scales, and scored pathologically using standard H & E histological analysis (Brown, A., et al., *Lab Invest.* 45:278 (1981), Lublin, F., et al., *J. Immunol.* 126:819 (1981), and Bernard, C. et al., *Eur. J. Immunol.* 16:655 (1976)). Animals are monitored for at least 100 days after transfer so that the number of relapses can be determined.

Example 9

Orally Induced Suppression of Proliferative Responses in SLJ Mice

Figure 4:
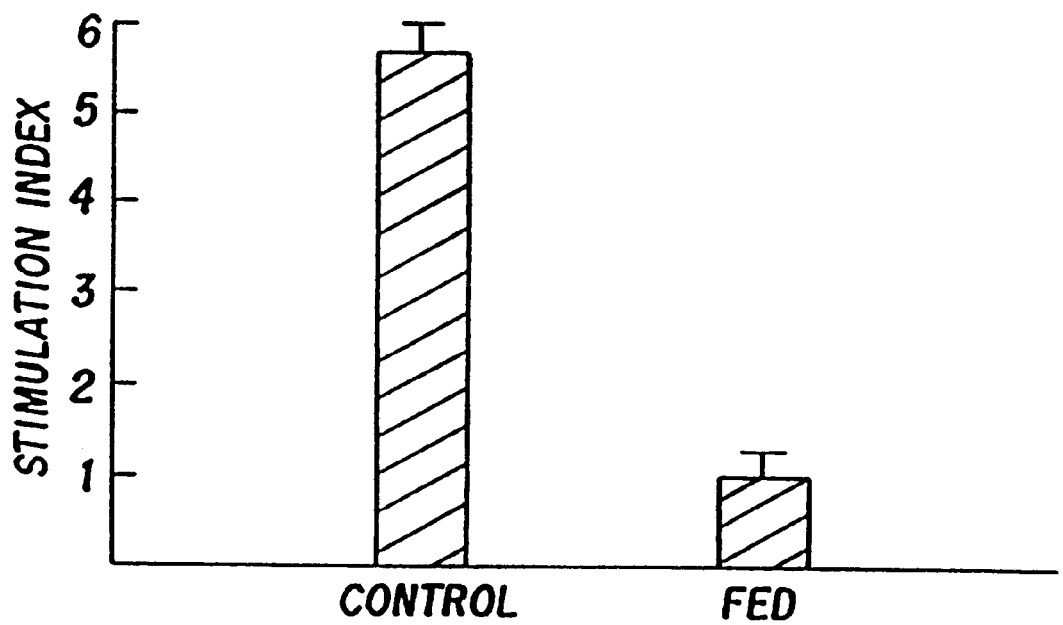
FIG. 4: orally-induced suppression of lymphoid cell proliferation in SJL mice. Animals were fed 400 μg MBP 7 times over a 2 week period and immunized with 400 μg MBP in CFA (0.6 mg/ml *M. tuberculosis*). Stimulation index is MBP-induced proliferation divided by background.

The feeding of 400 μg MBP every other day for two weeks (total of seven separate feedings) prior to immunization with 400 μg MBP in CFA (0.6 mg/ml *M. tuberculosis*) suppresses the proliferation of lymph node cells in response to MBP immunization. The results are shown in FIG. 4. This Figure depicts the control results versus the feeding results as a function of the MBP-induced proliferation divided by background (Stimulation Index).

The invention is not limited to those modes and embodiments of this application and embodiments that have been described above. It encompasses any modifications that result in the suppression of autoimmune diseases as taught by the present invention. These equivalents are included within the field of protection defined by the claims.

Example 10

Adoptive Transfer of Protective Resistance to EAE Development from MBP Fed Donor Rats to Naive Syngeneic Recipient Rats Donor rats were fed with either MBP or BSA, 1 mg×5 times, at 3–4 day intervals and sacrificed 4 days after the final feeding. Mesenteric lymph node cells (LNC) and spleen cells were harvested and injected intraperitoneally either immediately or after activation with concanavalin-A (Con-A), 1.5 μg/ml, in proliferation media for 48 hrs. The number of cells injected for adoptive transfer experiments were as follows: 120×10$^6$ for whole LNC population, either activated or not; 60×10$^6$ for CD3 depleted LNC; 80×10$^6$ for CD4 depleted population; and 95×10$^6$ for CD8 depleted LNC. Recipient Lewis rats were immunized with MBP/CFA 4 hrs later for the induction of EAE. The ability to transfer resistance to development of EAE from fed donor rats to naive syngeneic recipient rats is shown in Table VII. LNC obtained from unfed rats or from bovine serum albumin (BSA) fed donor rats failed to transfer protection against EAE. However, both spleen cells or mesenteric (MES) lymph node cells obtained from MBP fed donors were capable of transferring relative protection against EAE induced in the recipients, demonstrating 50% and 57% suppression of disease, respectively. The mean maximal severity of disease was also reduced markedly in recipients of either spleen cells or mesenteric lymph nodes cells obtained from MBP fed donor rats. These results demonstrate that the oral tolerance to EAE induction is of cellular origin and that the cells responsible for protection are found to be concentrated in both the mesenteric lymph nodes and the spleen.

TABLE VII

Adoptive transfer of protection against EAE using LNC obtained from either fed or untreated donor rats.

| Rats Fed with | Donors Source of LNC | EAE in Recipients Incidence | Mean Max. severity |
|---|---|---|---|
| None | SPC | 6/7 | 2.5 ± 0.3 |
|  | Mes.LNC | 5/5 | 2.6 ± 0.4 |
| BSA | SPC | 4/4 | 2.4 ± 0.2 |
|  | Mes.LNC | 5/5 | 2.6 ± 0.3 |
| MBP | SPC | 4/8* | 1.6 ± 0.2* |
|  | Mes.LNC | 4/7* | 1.7 ± 0.2* |

Lewis rats were fed with either MBP or BSA five times, 1 mg per feeding at 3 day intervals, or remained untreated. The rats were then sacrificed and their spleens and mesenteric lymph nodes were removed. The LNC were harvested and activated for 48 hours in the presence of Con-A. The lymphoblasts were collected, washed three times, and injected intraperitoneally into naive syngeneic rats. The recipient rats were challenged 4 hours later with MBP/CFA for the induction of EAE. The disease was scored daily from day 10 (*Results are statistically significant, p < 0.05).

Example 11

Identification of the Lymph Node Cell Subpopulation which mediates Resistance to EAE Con-A activated spleen cells (SPC) obtained from MBP fed donor rats were transferred to naive syngeneic rats either before or after depleting either T cells, helper T lymphocytes (CD4) or suppressor/cytotoxic T lymphocytes (CD8). For depletion of CD3, CD4 and CD8 populations from spleen cells, negative selection was used. Petri dishes were coated overnight at 4° C. with 10 ml of $^1$/$_{1000}$ goat anti-mouse IgG+IgM antibodies (Tago) in PBS/BSA. The plates were then washed and coated with 3% fetal bovine serum in PBS for 30 min at 20° C. and washed again. Lewis LNC were stained with mouse anti-rat monoclonal antibodies (Serotec/Bioproducts) for CD3 (MRC, OX/38), CD4 (W3/25) or CD8 (OX/8) diluted $^1$/$_{100}$ in PBS. The cells were stained for 30 min on ice, washed and seeded on the precoated petri dishes, 15 million cells/5 ml PBS/plate, at 4° C. The supernatant containing nonadherent cells was aspirated gently 60 minutes later and centrifuged twice before cell examination and counting. This protocol yields cell populations of about 85–95% purity as examined in the fluorescence activated cell sorter by examining membrane immunofluorescence. The results are demonstrated in Table VIII. The results demonstrate that SPC are capable of transferring protection against EAE (50% incidence), whereas T cell depleted SPC lost their ability to protect recipient rats (group 2). Thus, it seems that the spleen cells which are capable of transferring protection are T lymphocytes. However, depletion of CD8 cells (group 4) results in failure of transferring protection, whereas CD4$^+$ depleted SPC showed a significant ability of protecting rats against EAE. Thus, it is evidence that the antigen specific T lymphocytes which are generated after oral administration of MBP and which are mediating resistance to disease induction are of the suppressor/cytotoxic subset.

TABLE VIII

Adoptive transfer of protection against EAE using depleted population of SPC.

| | SPC removed from | EAE in recipient rats | |
|---|---|---|---|
| Group | MBP fed donors | Incidence | Mean Max. Severity |
| 1 | Whole population | 2/4 | 1.7 ± 0.2* |
| 2 | CD3 depleted | 6/6 | 2.6 ± 0.4* |
| 3 | CD4 depleted | 2/6* | 1.2 ± 0.2* |
| 4 | CD8 depleted | 6/7 | 2.2 ± 0.3 |

Donor rats were fed with MBP, and treated as indicated in the legend of Table 1. The Con-A activated SPC were injected into naive recipient rats either before (group 1) or after depletion of certain subpopulation (groups 2-4). Depletion of CD3, CD4 or CD8 lymphocytes was done by coupling monoclonal IgG antibodies to the SPC and panning. Recipient rats were immunized with MBP/CFA and EAE was recorded from day 10 (*Results are statistically significant, p < 0.05).

Example 12

In vitro Suppression of Anti-MBP T Cell Responses by Addition of Lymph Node Cells from MBP Fed Rats Rats were immunized with MBP/CFA and their primed popliteal draining lymph nodes (PLNC) harvested nine days later. A single cell suspension was prepared by pressing the lymph nodes through a stainless steel mesh. A total of $10^5$ LNC were cultured with the indicated number of either irradiated (2000 Rads) or intact LNC derived from fed rats in quadriplicate in round bottomed 96-well plate (Costar). MBP and *Mycobacterium tuberculosis*, 50 μg/ml were added to the culture in a volume of 20 μl. The cultures were incubated for 80 hrs. and were pulsed with 1 μCi [$^3$H] TdR/well for the last 16 hours of culture. The cultures were harvested on an automatic cell harvester and read on a standard liquid scintillation counter.

Percent suppression of primed LNC (PLNC) proliferation was calculated by the following formula:

$$\% \text{ Suppression} = 100 \times 1 - \frac{\text{cpm (irradiated LNC from fed rat + PLNC + antigen)}}{\text{cpm (irradiated LNC from untreated rat + PLNC antigen)}}$$

Figure 5:
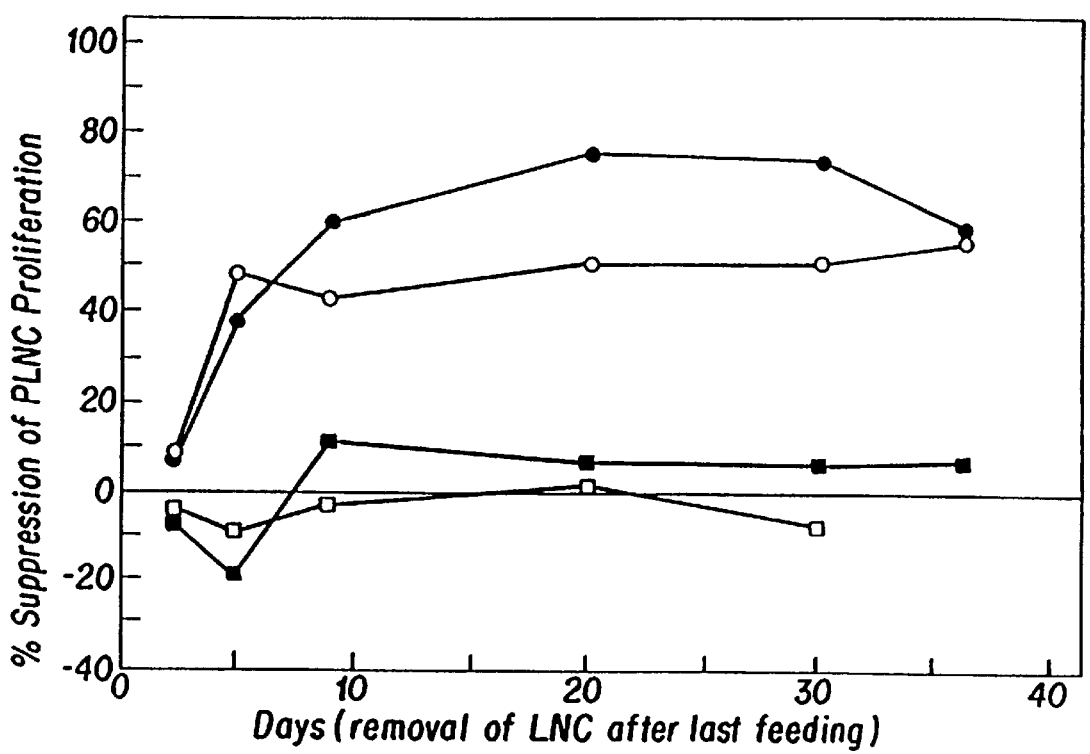
FIG. 5: antigen specific suppression of popliteal draining lymph node cells (PLNC) responses by spleen and mesenteric lymph node cells (LNC) obtained from myelin basic protein (MBP) fed rats. The results are expressed as percent suppression of PLNC to MBP (circles) as to *Mycobacterium tuberculosis* (squares). Closed circles or closed squares represent the response of spleen cells. Open circles or open squares represent the response of mesenteric lymph node cells.

The PLNC were cultured along with irradiated SPC or mesenteric LNC obtained from either naive or MBP fed rats in the presence of either MBP or *Mycobacterium tuberculosis*. The LNC obtained from MBP fed donor rats were examined on a different days after last feeding. Results are shown in FIG. 5. It is shown that within the time frame of the experiment, LNC obtained from fed rats did not affect the PLNC responses to *Mycobacterium tuberculosis*. However, both SPC and mesenteric LNC obtained from fed rats were able to suppress the PLNC proliferation to MBP. Antigen specific suppression of PLNC responses was greater using SPC than mesenteric LNC. Suppression is evident from day 5 to day 36 after the last feeding with MBP indicating that the induction of suppression is achieved soon after feeding and it is maintained for a relatively long period of time.

Thus, it seems that LNC obtained from rats rendered to be tolerized to EAE induction are antigen-specific lymphocytes which are capable of suppressing cellular immune responses only to the antigen used for feeding.

Example 13

Suppression of Anti-MBP Responses of PLNC in the Presence of Irradiated SPC and its Subpopulations, Obtained from a MBP Fed Rat To examine the subpopulation of SPC responsible for suppression, SPC were obtained from MBP fed rat 20 days after the last feeding, depleted of certain lymphocyte populations, irradiated and mixed with PLNC obtained from MBP/CFA immunized rat together with MBP. Popliteal and splenic LNC were seeded at a concentration of $10^7$ cells per ml petri dish either alone or irradiated (2000 Rads) together with other PLNC as indicated. The cultures were maintained in proliferation media, with or without antigen (20 μg/ml), for 3 days in an incubator and then harvested. The diluted supernatants were used to examine the in vitro production and secretion of IgG antibody and were measured for antibody production using an ELISA test. Microtiter plates were incubated with 0.1 ml per well of 10 μg antigen/ml in doubled distilled water. Plates were incubated for 18 hrs. at 25° C. After 3 washes with PBS/tween-20 (Bio-Rad), pH 7.5, plates were incubated with 3% BSA/PBS for 2 hrs. at 37° C., washed twice and a 100 μl of diluted serum was added in quadruplicate. The plates were incubated for 2 hrs. at 37° C. After three rinses with PBS/tween-20, plates were incubated with 100 μl/well of peroxidase-conjugated goat anti-rat IgG antibody (Tago, USA) diluted 1:1000 in 1% BSA/PBS for 1 hr. at 25° C. Color reaction was obtained by exposure to D-phenylenediamine (0.4 mg/ml phosphate citrate buffer, pH 5.0) containing 30% $H_2O_2$. The reaction was stopped by adding 0.4N $H_2SO_4$ and the OD 492 nm was read on an ELISA reader. The results shown in Table IX represents the percent suppression of the antigen proliferation of PLNC in the presence of SPC obtained from MBP fed rats compared to their responses to MBP in the presence of SPC obtained from intact rats. It is demonstrated that SPC obtained from MBP fed rats (group 1) suppresses the responses of PLNC to MBP (70%). Depletion of T cells (group 2) or suppressor/cytotoxic T lymphocytes (group 3) abrogates suppression. However, depletion of helper T lymphocytes (CD4, group 4) enhances the inhibition of the anti-MBP proliferation response of the PLNC. Diluting the CD4 depleted SPC results in decreasing of suppression from 96% (in the 1:1 ratio) to 18% (in the 1:100 ratio of SPC:PLNC).

These results suggest that the cells responsible for both disease inhibition and antigen-specific cellular responses in vitro are of the T cell origin and that they are suppressor/cytotoxic T lymphocytes.

TABLE IX

Suppression of anti-MBP responses of PLNC in the presence of irradiated SPC and its subpopulations, obtained from MBP fed rats.

| Group | SPC removed from MBP fed rats | SPC:PLNC ratio | % Suppression of PLNC responses to MBP |
|---|---|---|---|
| 1 | Whole population | 1:1 | 70 |
| 2 | CD3 depleted | 1:1 | −13 |
| 3 | CD8 depleted | 1:1 | −30 |
| 4 | CD4 depleted | 1:1 | 96 |
| | " | 1:10 | 32 |
| | " | 1:50 | 35 |
| | " | 1:100 | 18 |

TABLE IX-continued

Suppression of anti-MBP responses of PLNC in the presence of irradiated SPC and its subpopulations, obtained from MBP fed rats.

| Group | SPC removed from MBP fed rats | SPC:PLNC ratio | % Suppression of PLNC responses to MBP |
|---|---|---|---|

Spleens were removed from MBP fed Lewis rats, then cells were harvested, irradiated and seeded along with responder PLNC removed from MBP/CFA immunized syngeneic rats. The SPC were used as untreated cells or depleted of CD3, CD4 or CD8 T lymphocytes using the appropriate monoclonal antibodies for coupling and then panning. Results are expressed as percent suppression of PLNC responses to MBP and are relative to the PLNC responses in the presence of irradiated SPC removed from unfed rats.

Example 14

Figures 6A, 6B:
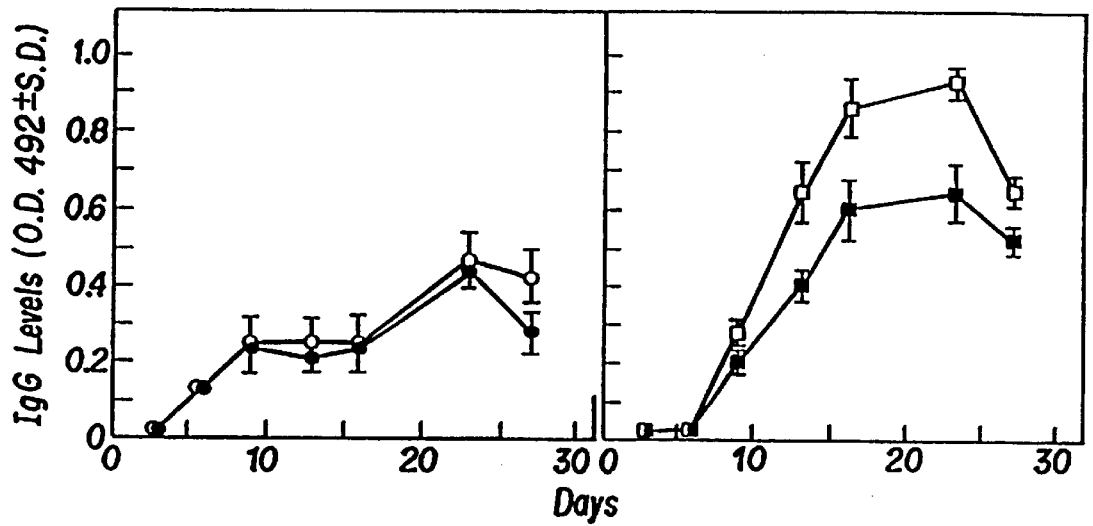
FIG. 6A and FIG. 6B: specific suppression of IgG responses to MBP after oral MBP feeding. Rats were bled at intervals and sera examined for anti-OVA (FIG. 6A, open circles) or anti-MBP (FIG. 6B, open squares) antibodies. These sera were compared to sera obtained from unfed and challenged animals (closed symbols). Results are expressed as ELISA O.D. 492 levels±S.D.

Humoral Suppression of Anti-MBP IgG Production Induced by Oral Tolerance to MBP Lewis rats were either fed with MBP or left untreated and then challenged with MBP mixed with ovalbumin (OVA) emulsified in CFA. The rats were then bled at various intervals, and sera was examined for anti-OVA or anti-MBP antibodies. As shown in FIG. 6a, the IgG serum levels to OVA were not affected in MBP fed rats, whereas IgG serum levels to MBP were decreased in MBP fed rats (6b).

Example 15

Determination of the Cell Type Responsible for the Suppression of IgG Production In Vitro Lewis rats were fed with MBP or remained unfed and then were immunized with MBP+OVA/CFA. The PLN were removed 12 days later, and the PLNC were cultured for 3 days in the presence of either MBP or OVA, the supernatants were collected, diluted 1:20 and examined for their IgG contents. As shown in Table X, PLNC, which were obtained from fed rats (group 2) and cultured in vitro with MBP, responded less in terms of IgG production to MBP in comparison to PLNC obtained from unfed rats (group 1, 45% suppression). The production of anti-OVA IgG production in PLNC from the same rats was not affected, (group 4 vs. 5). Moreover, mixing irradiated PLNC obtained from MBP fed and immunized rats with PLNC of immunized rats cultured together with MBP, decreased the antibody production of the later (group 3, 35% suppression), whereas the antibodies titers against OVA was not affected (group 6). In addition, removal of CD8+ cells abrogated the suppression of anti-MBP antibodies demonstrating that, as in adoptive transfer and proliferative responses, CD8+ cells were responsible for suppression.

TABLE X

| | | | IgG Levels in Supernatants | | |
|---|---|---|---|---|---|
| Group | Responder Cells | Modulator Cells | In Vitro Stimulation | O.D. 492 Values ± S.D. | % Suppression of IgG Production |
| 1 | Immunized | — | MBP | 0.56 ± 0.06 | — |
| 2 | MBP Fed and Immunized | — | MBP | 0.31 ± 0.01 | 45 |
| 3 | Immunized | MBP Fed | MBP | 0.36 ± 0.04 | 35 |
| 4 | Immunized | MBP Fed and Immunized and Immunized CD8+ depleted | MBP | 0.55 ± 0.04 | 0 |
| 5 | Immunized | — | OVA | 0.17 ± 0.03 | — |
| 6 | MBP Fed and Immunized | — | OVA | 0.18 ± 0.02 | 0 |
| 7 | Immunized | MBP Fed and Immunized | OVA | 0.21 ± 0.04 | 0 |

Rats were immunized with MBP + OVA and CFA (some 3 days after the fifth feeding of MBP). Twelve days later their PLNC were removed and cultured together with MBP (groups 1–4) or with OVA (groups 5–7) for three days. In some groups, irradiated PLNC obtained from MBP fed and immunized rats were irradiated and cultured along with immunized PLNC in the presence of MBP (group 3) or in the presence of OVA (group 7). The supernatants of these stimulations were collected, diluted and IgG levels determined by ELISA.

Example 16

Identification of the MBP Region which Actively Suppresses EAE using Overlapping Synthetic Polypeptides of MBP Overlapping fragments of the amino acid 1–37 fragment of guinea pig myelin basic protein were synthesized using solid phase peptide technique. Houghten, R., *Proc. Natl. Acad. Sci.* USA 82:5131–5135 (1985). These fragments were then administered orally in equimolar concentrations to 15 mg of whole myelin basic protein. They were administered on day −7, −5, and −2 prior to immunization. Animals were then challenged with basic protein in Freund's adjuvant according to established procedures and scored.

Animals were scored for mortality, presence of disease, and disease severity. As shown in Table XI, 6/6 control animals became ill with a mortality of 3/6. In animals receiving overlapping peptide fragments, there was decreased mortality using all fragments, except for fragment 1–10. When viewed in terms of disease severity, the region of the molecule between amino acids 5 and 20 shows the most pronounced diminution of disease. These results demonstrate that in the amino acid region 1–37 which itself is a suppressogenic fragment, specific regions of the molecule may be more or less suppressive when administered orally.

TABLE XI

| | EAE Mediated by MBP/CFA | | |
|---|---|---|---|
| Fragment | Incidence of Disease | Mean Max. Score | Mortality |
| Control (PBS) | 6/6 | 3.8 | 3/6 |
| 1–10 | 5/5 | 3.8 | 4/5 |
| 5–15 | 4/5 | 2.1 | 1/5 |
| 11–20 | 4/5 | 2.0 | 0/5 |
| 16–25 | 4/5 | 2.6 | 0/5 |
| 21–30 | 5/5 | 3.0 | 1/5 |

TABLE XI-continued

| | EAE Mediated by MBP/CFA | | |
|---|---|---|---|
| Fragment | Incidence of Disease | Mean Max. Score | Mortality |
| 26–36 | 4/6 | 2.6 | 1/6 |
| 31–37 | 5/6 | 3.3 | 0/6 |

Overlapping fragments of the 1–37 region of guinea pig myelin basic protein were synthesized using solid phase peptide technique. These fragments were then administered orally in equimolar concentrations to 15 mg of whole myelin basic protein. They were administered on day −7, −5, and −2 prior to immunization. Animals were then challenged with basic protein in Freund's adjuvant according to established procedures and scored.

Example 17

Demonstration that Oral Route of Administration of a Protein Antigen Determines to which Fragment there is an Immune Response Animals were given whole myelin basic protein, either immunized in the foot pad with Freund's adjuvant or administered orally. Seven to 10 days thereafter, spleen and lymph node cells were removed and restimulated in vitro with different fragments of the basic protein molecule.

As shown in Table XII, when myelin basic protein is administered peripherally in Freund's adjuvant, the primary response is to the 44–89 encephalitogenic region as measured by proliferation. However, as shown in Table XIII, when it is administered orally, the primary response is to fragment 1–37, the non-encephalitogenic suppressor determinant.

TABLE XII

Proliferation to MBP fragments in Lewis rats immunized with whole MBP.

| | Counts Per Minute | Stimulation Index |
|---|---|---|
| Background | 3,292 | — |
| Whole MBP | 10,142 | 3.1 |
| MBP fragment 1–37 | 3,360 | 1.0 |
| MBP fragment 44–89 | 10,054 | 3.0 |

Animals were immunized in hind foot pads with 50 $\mu$g MBP in CFA. Ten days later lymph nodes were removed and stimulated in vitro with 10 $\mu$g MBP or equimolar amounts of MBP fragments.

TABLE XIII

Proliferation to MBP fragments in Lewis rats fed whole MBP orally.

| Source of LNC | Whole MBP | 1–37 | 44–89 |
|---|---|---|---|
| SPC | 5.10 ± 1.6 | 5.05 ± 1.8 | 2.41 ± 0.9 |
| Mes.LNC | 8.61 ± 1.9 | 9.88 ± 1.5 | 3.53 ± 0.8 |
| Cervicals | 4.58 ± 1.3 | 6.42 ± 0.9 | 2.51 ± 0.6 |

Animals were fed 1 mg of whole MBP x3, then cells removed from various organs 15 days following feeding and proliferation measured. Results are expressed as the change in cpm × $10^{-3}$ as compared to cells cultured alone.

Example 18

Figure 7A:
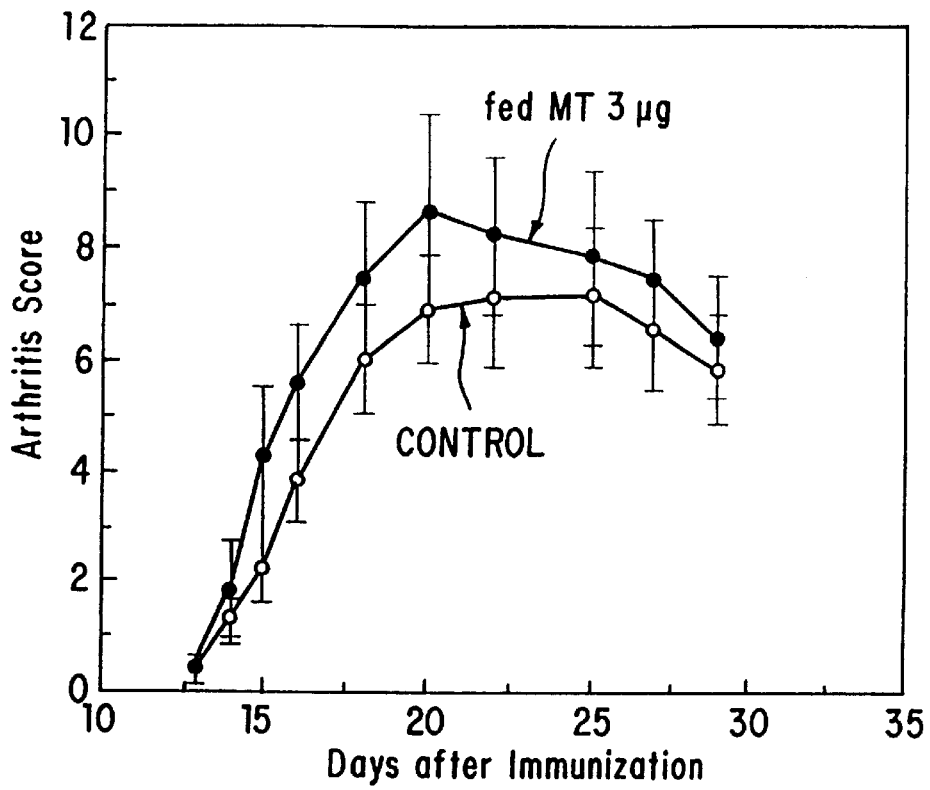
FIG. 7: Lewis rats were fed with MT (Figure A) or CII (Figure B), on day −7, −5 and −2. Animals were then intradermally injected with CFA containing 10 mg/ml of MT at the base of the tail on day 0 for induction of AA. Beginning on day 13, animals were examined for clinical signs of AA and were scored individually, the "arthritis score" reflects the average arthritis score (sum of the four paws) from 5–10 individual rats in each group for each time point.

The Effect of Feeding Mycobacterium tuberculosis or Type II Collagen on Adjuvant Arthritis Since AA is induced by CFA containing M. tuberculosis, an initial approach in studying the problem was to feed animals with various dosages of MT. Unexpectedly, no suppression of disease was observed as measured by incidence of arthritic limbs, day of onset, or maximum arthritis score over a wide dose range, in which 3 $\mu$g, 30 $\mu$g, 300 $\mu$g or 3 mg of MT was 10. administered on days −7, −5 and −2 prior to immunization. Representative data in which animals were pretreated with 3 $\mu$g is shown in FIG. 7A.

Figure 7B:
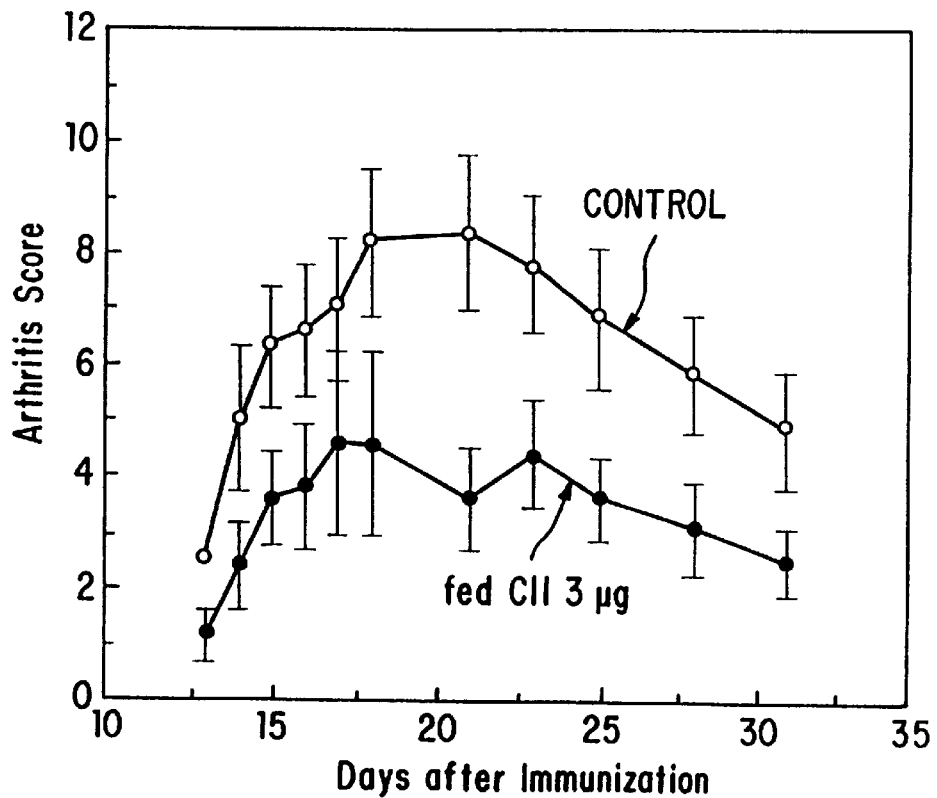

Based on investigations which reported the development of autoimmunity to collagen in rats with AA (Trentham, D. E. et al., J. Clin. Invest. 66:1109 (1980)), the effect of orally administering type II collagen on AA was studied. As shown in FIG. 7B and Table XIV, prefeeding rats with CII significantly suppressed AA in a dose-dependent manner with the most pronounced effects seen in groups fed 3 $\mu$g or 30 $\mu$g of CII. Occasional suppression was seen at 300 $\mu$g. In animals fed 3 $\mu$g or 30 $\mu$g, the incidence of arthritic limbs was less and the disease was midler as measured by the maximum arthritis score. The onset of the disease was also delayed in animals fed 3 $\mu$g of CII. To determine whether oral administration of CII had non-specific suppressive effects on experimental autoimmune diseases, an identical dose-range of CII was fed to animals immiunized with myelin basic protein in CFA for the induction of experimental autoimmune encephalomyelitis (EAE) (Higgins, P. J. et al., J. Immunol. 140:440 (1988)). No effect on the development of EAE was observed following feeding CII.

TABLE XIV

The Effect of Feeding Collagen II on Adjuvant Arthritis

| pre-treatment | arthritic limbs | day of onset | maximum arthritis score |
|---|---|---|---|
| control (buffer alone) | 40/40 | 13.1 ± 0.3 | 9.1 ± 1.2 |
| CII 0.3 $\mu$g | 19/20 | 12.6 ± 0.2 | 9.6 ± 1.4 |
| CII 3 $\mu$g | 26/36[a] | 15.3 ± 1.1[b] | 5.1 ± 0.9[c] |
| CII 30 $\mu$g | 30/40[a] | 13.7 ± 0.4 | 6.2 ± 0.7[b] |
| CII 300 $\mu$g | 39/40 | 13.1 ± 0.3 | 7.7 ± 0.9 |
| CII 1 mg | 19/20 | 12.4 ± 0.2 | 9.0 ± 1.6 |

Lewis rats were fed with either buffer (control group), or various doses of CII three times on days −7, −5 and −2, and intradermally injected on day 0 at base of the tail with CFA containing 1 mg of MT for the induction of adjuvant arthritis. The arthritis was evaluated every 2–3 days from day 12 to day 31. p-values represent CII fed groups vs. controls (PBS fed). ns = not significant.
[a] $p < 0.001$ vs. control
[b] $p < 0.05$ vs. control
[c] $p < 0.01$ vs. control

Example 19

Figure 8A:
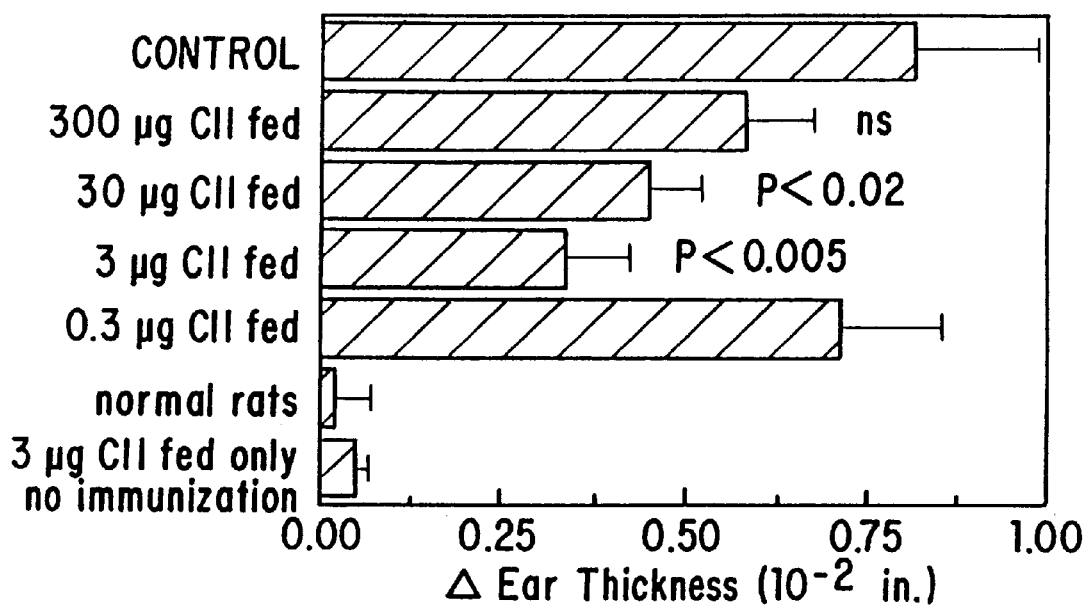
FIG. 8: Lewis rats were fed with either buffer alone (control), or varying dosages of CII as indicated, on days −7, −5 and −2. Animals were then immunized intradermally with CFA containing 10 mg/ml of MT at the base of the tail. One month later, animals were challenged with either 20 μg CII (Figure A), or 10 μg MT (Figure B). Ear thickness was measured prior to and 48 hours after injection. P values comparison of fed animals vs. control. ns=not significant.
Figure 8B:
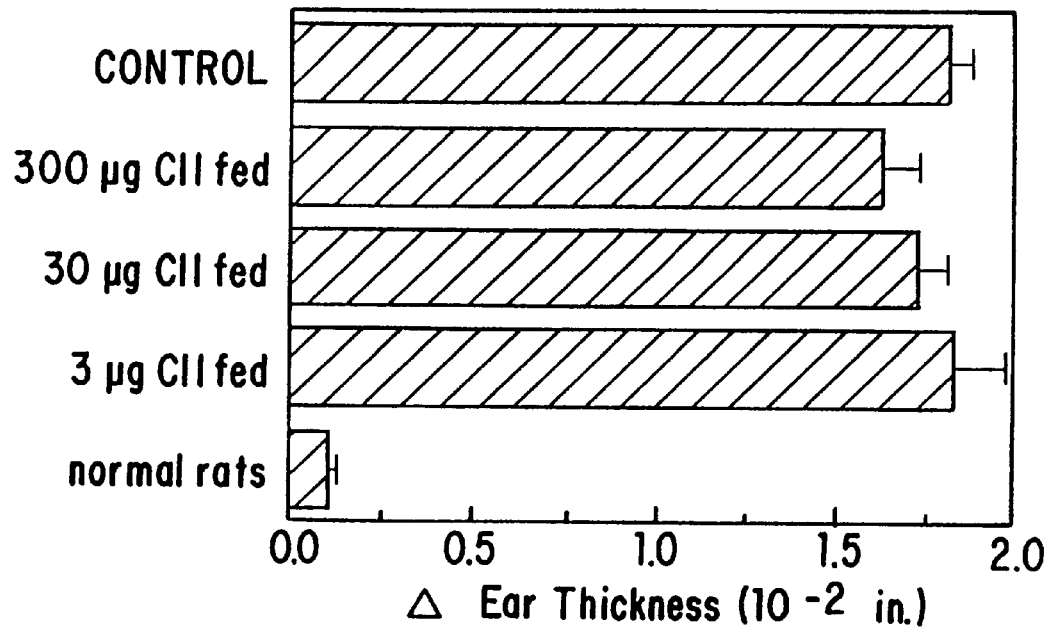
Figure 9:
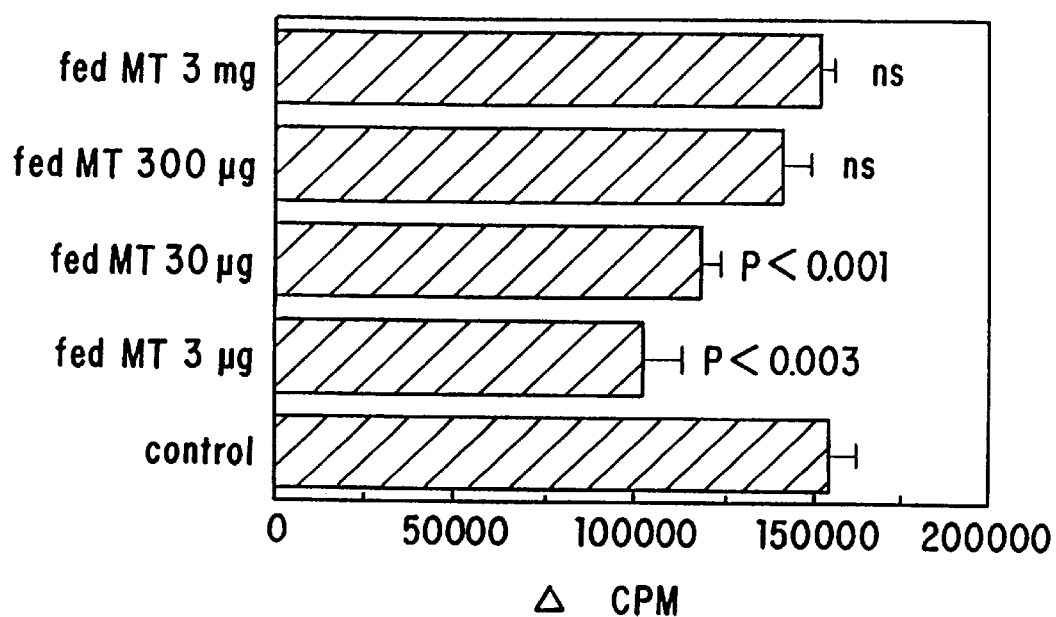
FIG. 9: Lewis rats were fed various dosages of MT on day −7, −5 and −2 and immunized on day 0 with 0.1 ml CFA at the base of the tail. Draining lymph nodes were collected 9 days later and proliferative responses measured.

Delayed Type Hypersensitivity Responses Following Oral Administration of Type II Collagen and MT It has been reported that immunity to both CII and MT develops in AA (Trentham, D. E. et al., J. Clin. Invest. 66:1109 (1980)). DTH responses were performed to determine the effect of feeding CII on in vivo T cell responses to both MT and CII. As shown in FIG. 8A, animals immunized with CA develop DTH to CII although it is not as pronounced as DTH to MT (FIG. 8B). Furthermore, oral administration of CII reduced the DTH response to CII in animals with AA, whereas there was no effect on the DTH response to MT. The dose response range for suppression of DTH by CII was identical as for suppression of disease with CII, i.e., the most prominent suppression seen at 3 $\mu$g and 30 $\mu$g. Of note is that there was no sensitization to CII in animals that were only fed 3 $\mu$g without subsequent immunization. The suppression of cellular immune responses to MT following oral administration of the antigen was next examined. As shown in FIG. 9, the proliferative responses to MT were suppressed in animals fed with 3 μg and 30 μg MT. Similar suppression was observed as measured by DTH responses.

Example 20

Adjuvant Arthritis is Suppressed by Adoptive Transfer of T cells from CII Orally Tolerized Rats It was previously shown that suppression of EAE following oral administration of myelin basic protein can be adoptively transferred by splenic T cells from fed animals (Lider, O., et al., *J. Immunol.* 142:748–752 (1989)), and similar results in the autoimmune uveitis model have been obtained. As shown in Table XV, protection against AA was adoptively transferred to naive rats by splenic T cells from rats orally tolerized to CII. Protection was more pronounced when splenocytes were transferred on day −2 and when splenic T cells vs. B cells were transferred.

TABLE XV

The Effect of Feeding Non-cartilaginous Collagens on Adjuvant Arthritis

| Pretreatment | Arthritic Limbs | Day of Onset | Maximum Arthritis Scores |
|---|---|---|---|
| Control (buffer alone) | 20/20 | 12.6 ± 0.7 | 9.7 ± 1.9 |
| CI 3 μg | 9/16[a] | 16.3 ± 3.6 | 5.2 ± 2.5[b] |
| CI 30 μg | 18/20 | 14.0 ± 1.5 | 4.2 ± 0.6[c] |
| CIII 3 μg | 18/20 | 14.4 ± 0.5[b] | 7.2 ± 2.0 |
| CIII 30 μg | 18/20 | 14.5 ± 0.6[b] | 6.3 ± 0.7 |

Lewis rats were fed with varying degrees of CI or CIII three times on days −7, −5, and −2 (control animals were fed buffer only). p-values represent fed vs. control. ns = not significant.
[a]$p < 0.01$ vs. control
[b]$p < 0.04$ vs. control
[c]$p < 0.001$ vs. control Example 21

Suppression of AA by Oral Administration of CII After Disease Onset

Figure 10:
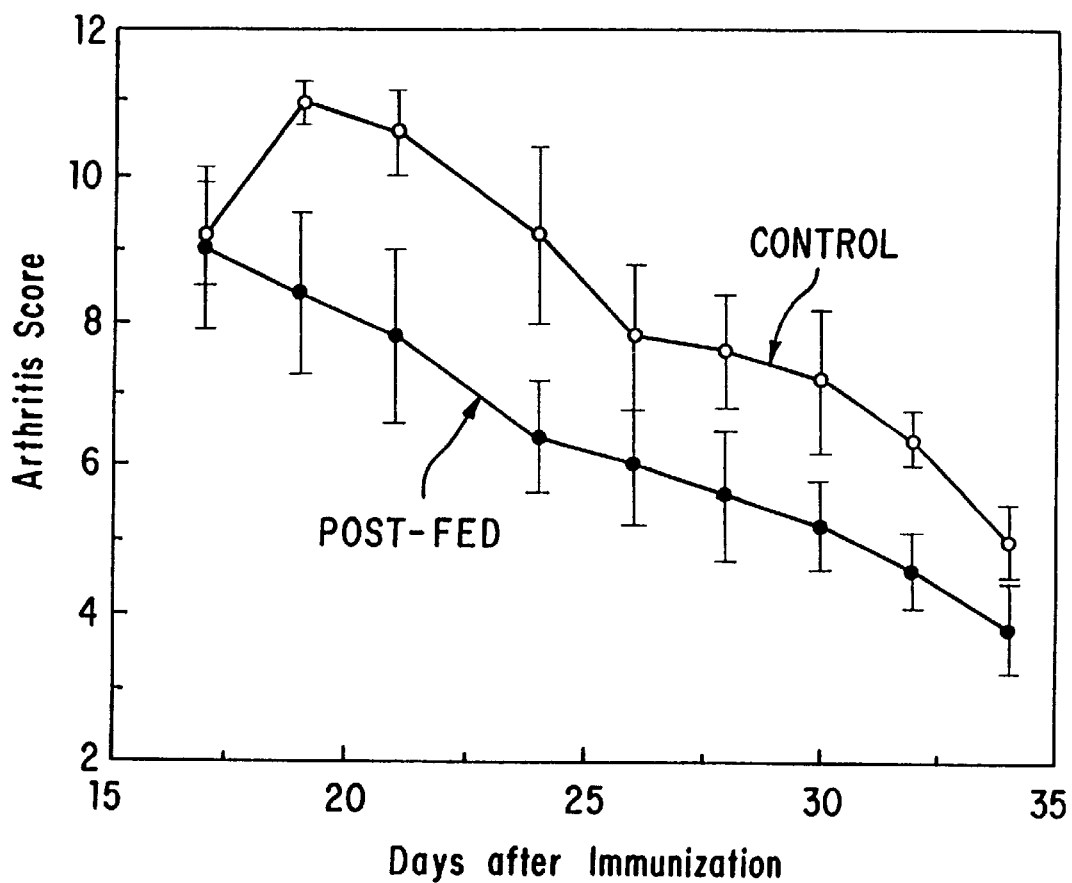
FIG. 10: Lewis rats were induced for arthritis by intradermal injection of CFA containing 10 mg/ml MT. Initial signs of arthritis appeared 13–14 days after disease induction. On day 17, animals were separated into two groups with matching severity of the disease. The control group remained untreated whereas the treated group received 3 μg CII orally three times per week at every other day intervals. The animals in both groups were scored for arthritis until day 34. Data are expressed as mean arthritis score±standard error.

In order to determine if feeding CII could ameliorate already established AA, animals were fed CII after the onset of disease. Initial signs of arthritis appeared 13–14 days after disease induction with CFA. On day 17, animals were separated into two groups with matching severity of the disease. The control group remained untreated whereas the treated group received 3 μg CII orally three times per week at every other day intervals. The animals in both groups were scored for arthritis until day 34. As shown in FIG. 10, animals treated with CII developed milder arthritis and recovered sooner than controls.

Example 22

The Effect of Feeding Non-cartilage Collagens on AA

Even though the molecular structure of CII is very closely related to other collagens, such as type I (CI) and type III collagen (CIII), the distribution of these collagens is quite different (Seyer, J. M., et al., In: *Textbook of Rheumatology*, 3rd ed. (Kelly et al., eds.), p. 22, Saunders, Philadelphia (1989)). Whereas CII is usually present in the cartilage of the joints, type I and type III collagens are found mostly in bones, skin, and other soft tissues. As shown in Table XVI, we found that oral administration of CI suppressed AA, as determined by incidence of arthritic limbs and disease severity, in the same dose range as CII. There was a delay in disease onset in animals fed CIII but no significant effect on disease severity. Oral administration of an irrelevant protein antigen, myelin basic protein, did not suppress AA.

TABLE XVI

Suppression of Adjuvant Arthritis by Adoptive Transfer of Splenocytes from CII-orally Tolerized Rats

| | Donor | Cells Transferred | Day of Transfer | Arthritic Limbs | Day of Onset | Arthritis Score |
|---|---|---|---|---|---|---|
| Experiment I | | | | | | |
| 1 | Normal | Splenocytes | 0 | 20/20 | 13.6 ± 0.2 | 11.2 ± 1.5 |
| 2 | CII fed | Splenocytes | 0 | 17/20 | 14.0 ± 0 | 6.6 ± 0.9[a] |
| 3 | Normal | Splenocytes | −2 | 20/20 | 13.8 ± 0.2 | 9.2 ± 1.6 |
| 4 | CII fed | Splenocytes | −2 | 8/20[b] | 15.2 ± 0.7[c] | 2.8 ± 0.5[c] |
| Experiment II | | | | | | |
| 1 | Normal | Splenocytes | −2 | 20/20 | 13.8 ± 0.2 | 9.0 ± 2.0 |
| 2 | CII fed | Splenic B cells | −2 | 20/20 | 13.8 ± 0.2 | 8.8 ± 1.1 |
| 3 | CII fed | Splenic T cells | −2 | 16/20 | 14.0 ± 0.5 | 4.0 ± 0.5[d] |

Donor Lewis rats were either unfed (normal) or pre-fed three times at 2–3 day intervals with 3 μg of CII. Spleens were taken 7 days after the last feeding and $1 \times 10^8$ splenocytes or nylon wool separated B (adherent) or T (nonadherent) cells were transferred by i.p. injection to each recipient which were induced for AA immediately or 2 days after adoptive transfer.
[a]$p < 0.05$, group 2 vs. group 1
[b]$p < 0.001$, group 4 vs. group 3
[c]$p < 0.01$, group 4 vs. group 3
[d]$p < 0.05$, group 3 vs. group 1

The lymphocyte proliferation and DTH experiments above indicated that oral administration of MT suppressed cellular immune responses against MT without inhibition of clinical disease. Nonetheless, cellular immunity to MT was not profoundly suppressed by oral tolerance and it may be that regimens that had a greater effect on suppressing MT immunity would suppress disease. In this regard, others have shown suppression of AA by administering the 65 kd HSP in oil (Billingham, M. E. J., et al., *J. Exp. Med.* 171:339 (1990) or by administering MT intradermally or intravenously (Larsson, P., et al., *J. Cell. Biochemistry* 40:49 (1989); Gery, I., et al., *Int. Arch. Allergy* 31:57 (1967)).

Suppression of AA by oral administration of CII suggests either that pathogenic immunity to CII develops in AA or that there are cross-reactive epitopes between MT and CII. Of note is that CII T cell lines were reported to have a minor effect in ameliorating AA by T cell vaccination (Holoshitz, J., et al., *Science* 219:56 (1983) and there was slight suppression of CIA by the 65 kd HSP (Billingham, M. E. J., et al., *J. Exp. Med.* 171:339 (1990)). Some investigators have reported suppression of AA by intravenous administration of CII (Phadke, K., et al., *Arthritis Rheum.* 27:797 (1984)) although this has not been uniformly found (Cremer, M. A., et al., *J. Immunol.* 131:2995 (1983)). Our studies suggest that the inability of investigators to demonstrate suppression of AA by i.v. administration of CII (Cremer, M. A., et al., *J. Immunol. 131:2995* (1983)) may relate to the use of too large a dose, viz., 1 mg. In preliminary experiments, some cross-reactivity between MT and CII has been found in proliferation assays although it remains undefined as to whether the suppression of AA by oral administration of CII relates to cross-reactivity between MT and CII. Amino acid sequence homology between chicken type II collagen and peptide 180–188 of the 65 kd heat shock protein of MT, which has been reported to stimulate clones mediating arthritis in rats (van Eden, W., et al., *Nature* 331:171 (1988)) has not been found. Recently, a 26-amino acid sequence from CII has been reported to suppress collagen induced arthritis (Myers, L. K., et al., *J. Exp. Med.* 170:1999 (1989)), however, no homologies between this peptide and the 65 kd peptide can be located. Clearly, given the size of both MT and CII, cross-reactive epitopes may exist which are not easily identified. Alternatively, MT may induce joint damage that leads to a pathogenic immune response to CII.

It has been demonstrated that active suppression is generated following oral administration of antigen (Ngan, J., et al., *J. Immunol.* 120:861 (1978); Mattingly, J. A., et al., *J. Immunol.* 125:1044 (1980); Mattingly, J. A., *Cell. Immunol.* 86:46 (1984); Zhang, Z., et al., *Cell. Immunol.* 104:426 (1987)), and that EAE may be suppressed by adoptive transfer of CD8+ T cells from orally tolerized animals (Lider, O. et al., *J. Immunol.* 142:748–752 (1989)).

Example 23

Treatment of Multiple Sclerosis Patients

The medication used for treatment is a bovine myelin extract prepared by BioPure, Boston, Mass. Bovine myelin is non-toxic when administered to animals and is effective in ameliorating chronic relapsing EAE. BioPure's bovine myelin is prepared on a sucrose gradient via density centrifigation using a Sharples centrifuge and analyzed by SDS page electrophoresis. The myelin is extracted from bovine brains obtained from local slaughter houses in Massachusetts and tested for purity and batch to batch standardization by agarose gel electrophoresis, protein determination, lipid analysis, amino acid determination, and immunologic reactivity. It is also tested for the presence of bacteria and viruses.

The myelin is administered to patients with multiple sclerosis in 100 mg capsules given three times per day for a total dose of 600 mg/day.

Example 24

Treatment of Autoimmune Arthritis Patients

The type II collagen used for treatment is a CII preparation obtained from Genzyme Corporation, Boston, Mass. (soluble chicken type II collagen). This preparation is effective in ameliorating adjuvant arthritis.

The CII is administered orally to patients with autoimmune arthritis in a dose of 10 $\mu$g to 100 mg per day. The CII is administered in a dry form or dissolved in a liquid (and volume) the patient is able to tolerate. In a preferred embodiment, a total dose of 100 $\mu$g up to 30 mg per day is administered. Such dosage may be administered in multiple doses so as to provide the patient with the total daily dose. In a preferred embodiment, such multiple dosage is three times per day.

All references cited herein are fully incorporated herein by reference. Having now fully described the invention, it will be understood by those with skill in the art that the scope may be performed within a wide and equivalent range of conditions, parameters and the like, without affecting the spirit or scope of the invention or any embodiment thereof.

What is claimed is:

1. A method for treating rheumatoid arthritis in a subject, comprising suppressing an autoimmune response associated with said arthritis by orally administering to said subject a composition comprising a therapeutically effective amount of a fragment or analog of collagen that is effective to suppress said response, said collagen being selected from the group consisting of collagen type I, collagen type II, and collagen type III.

2. The method of claim 1 wherein the therapeutically effective amount is from about 10 $\mu$g to about 100 mg per day.

3. The method of claim 1 wherein the therapeutically effective amount is from about 100 $\mu$g to about 30 mg per day.

4. The method of claim 1 wherein said collagen is solubilized.

5. A method for treating rheumatoid arthritis in a subject, comprising suppressing an autoimmune response associated with said arthritis by orally administering to said subject a composition comprising a therapeutically effective amount of a fragment of collagen that is effective to suppress said response, wherein said collagen is selected from the group consisting of collagen type I, collagen type II, and collagen type III.

6. The method of claim 5 wherein the therapeutically effective amount is from about 10 $\mu$g to about 100 mg per day.

7. The method of claim 5 wherein the therapeutically effective amount is from about 100 $\mu$g to about 30 mg per day.

8. The method of claim 5 wherein said collagen is solubilized.

9. A method for treating rheumatoid arthritis in a subject, comprising suppressing an autoimmune response associated with said arthritis by orally administering to said subject a composition comprising a therapeutically effective amount of an analog of collagen that suppresses said response, wherein said collagen is selected from the group consisting of collagen type I, collagen type II, and collagen type III.

10. The method of claim 9 wherein the therapeutically effective amount is from about 10 $\mu$g to about 100 mg per day.

11. The method of claim 9 wherein the therapeutically effective amount is from about 100 $\mu$g to about 30 mg per day.

12. The method of claim 9 wherein said collagen is solubilized.

13. A method for suppressing autoimmune response associated with rheumatoid arthritis in a subject, comprising orally administering to said subject an amount of an immunosuppressive fragment of collagen effective to suppress said autoimmune response, wherein said collagen is selected from the group consisting of collagen type I, collagen type II, and collagen type III.

14. The method of claim 13 wherein the therapeutically effective amount is from about 10 $\mu$g to about 100 mg per day.

15. The method of claim 13 wherein the therapeutically effective amount is from about 100 $\mu$g to about 30 mg per day.

16. The method of claim 13 wherein said collagen is solubilized.

17. A method for suppressing autoimmune response associated with rheumatoid arthritis in a subject, comprising orally administering to said subject an amount of an immunosuppressive analog of collagen effective to suppress said autoimmune response, wherein said collagen is selected from the group consisting of collagen type I, collagen type II, and collagen type III.

18. The method of claim 17 wherein the therapeutically effective amount is from about 10 μg to about 100 mg per day.

19. The method of claim 17 wherein the therapeutically effective amount is from about 100 μg to about 30 mg per day.

20. The method of claim 17 wherein said collagen is solubilized.

* * * * *